(12) United States Patent
Sharma et al.

(10) Patent No.: US 9,579,408 B2
(45) Date of Patent: Feb. 28, 2017

(54) PET/SPECT AGENTS FOR APPLICATIONS IN BIOMEDICAL IMAGING

(75) Inventors: Vijay Sharma, Wildwood, MO (US); Jothilingam Sivapackiam, St. Louis, MO (US); David Piwnica-Worms, Houston, TX (US)

(73) Assignee: Washington University, Saint Louis, MO (US)

(*) Notice: Subject to any disclaimer, the term of this patent is extended or adjusted under 35 U.S.C. 154(b) by 0 days.

(21) Appl. No.: 13/984,723

(22) PCT Filed: Feb. 10, 2012

(86) PCT No.: PCT/US2012/024752
§ 371 (c)(1),
(2), (4) Date: Aug. 7, 2014

(87) PCT Pub. No.: WO2012/109611
PCT Pub. Date: Aug. 16, 2012

(65) Prior Publication Data
US 2014/0343260 A1 Nov. 20, 2014

Related U.S. Application Data

(60) Provisional application No. 61/441,732, filed on Feb. 11, 2011.

(51) Int. Cl.
*A61K 51/04* (2006.01)
*C07B 59/00* (2006.01)
(Continued)

(52) U.S. Cl.
CPC ............ *A61K 51/0478* (2013.01); *C05D 9/02* (2013.01); *C07B 59/001* (2013.01);
(Continued)

(58) Field of Classification Search
None
See application file for complete search history.

(56) References Cited

U.S. PATENT DOCUMENTS

| | | |
|---|---|---|
| 5,186,923 A | 2/1993 | Piwnica-Worms et al. |
| 5,324,502 A | 6/1994 | Green |

(Continued)

FOREIGN PATENT DOCUMENTS

| | | |
|---|---|---|
| WO | 93/19787 | 10/1993 |
| WO | WO-93-19787 | * 10/1993 |

(Continued)

OTHER PUBLICATIONS

Silverman, "The Organic Chemistry of Drug Design and Drug Action", p. 19-21, 1992.*

(Continued)

*Primary Examiner* — Jianfeng Song
(74) *Attorney, Agent, or Firm* — Zackson Law LLC; Saul L. Zackson

(57) ABSTRACT

Tracers that can be used for PET or SPECT imaging of the distribution of Pgp are disclosed. The tracers are metalloprobes that can comprise a radioactive metal ion such as $^{67}$Ga or $^{68}$Ga. Methods of synthesizing the tracers, and methods of imaging heart and other tissues are also disclosed. The tracers can be used to obtain high signal-to-background ratios for imaging tissues in vivo such as heart or tumor tissue. In various embodiments, disclosed tracers can exhibit, a) enhanced first pass extraction into heart tissue compared to presently available probes, b) linearity with true blood flow, c) enhanced detection of myocardial viability compared to presently available probes, d) reduced liver retention compared to presently available probes, and e) more efficient clearance from non-cardiac and adjoining tissues compared to presently available probes.

6 Claims, 5 Drawing Sheets

(51) Int. Cl.
  *C07C 251/24* (2006.01)
  *C05D 9/02* (2006.01)
  *C07F 5/00* (2006.01)
(52) U.S. Cl.
  CPC .......... *C07B 59/002* (2013.01); *C07C 251/24* (2013.01); *C07F 5/003* (2013.01)

(56) References Cited

U.S. PATENT DOCUMENTS 5,403,574 A 4/1995 Piwnica-Worms et al.
5,407,653 A 4/1995 Piwnica-Worms et al.

FOREIGN PATENT DOCUMENTS

WO WO9640108 A1 12/1996
WO 03/086476 10/2003
WO 2008/128058 10/2008

OTHER PUBLICATIONS

Bigott, H.M., et al. "Imaging multidrug resistance P-glycoprotein transport function using microPET with technetium-94m-sestamibi" Mol Imaging. Jan.-Mar. 2005;4(1):30-9.
Dothager, R.S., et al. "Cerenkov radiation energy transfer (CRET) imaging: a novel method for optical imaging of PET isotopes in biological systems" PLoS One. Oct. 11, 2010;5(10):e13300.
Harpstrite, S.E., et al. "Metalloantimalarials: targeting of P. falciparum strains with novel iron(III) and gallium(III) complexes of an amine phenol ligand" Inorg Chem. Apr. 7, 2003;42(7):2294-300.
Harpstrite, S.E., et al. "Metalloprobes: synthesis, characterization, and potency of a novel gallium(III) complex in human epidermal carcinoma cells" J Inorg Biochem. Oct. 2007;101(10):1347-53. Epub May 8, 2007.
Hsiao, Y.M., et al. "Synthesis and biodistribution of lipophilic and monocationic gallium radiopharmaceuticals derived from N,N'-bis(3-aminopropyl)-N,N'-dimethylethylenediamine: potential agents for PET myocardial imaging with 68Ga" Nucl Med Biol. Jan. 2009;36(1):39-45.
Ocheskey, J.A., et al. "Synthesis, characterization, and molecular structure of a gallium(III) complex of an amine-phenol ligand with activity against chloroquine-sensitive Plasmodium falciparum strains" J Inorg Biochem. Jan. 15, 2003;93(3-4):265-70.
Piwnica-Worms, D., et al. "Single photon emission computed tomography and positron emission tomography imaging of multi-drug resistant P-glycoprotein—monitoring a transport activity important in cancer, blood-brain barrier function and Alzheimer's disease" Neuroimaging Clin N Am. Nov. 2006;16(4):575-89, viii.
Piwnica-Worms, D., et al. "Probing multidrug resistance P-glycoprotein transporter activity with SPECT radiopharmaceuticals" Curr Top Med Chem. 2010;10(17):1834-45.
Sharma, V., et al. "Novel gallium(III) complexes transported by MDR1 P-glycoprotein: potential PET imaging agents for probing P-glycoprotein-mediated transport activity in vivo" Chem Biol. May 2000;7(5):335-43.
Sharma, V., et al. "Effects of multidrug resistance (MDR1) P-glycoprotein expression levels and coordination metal on the cytotoxic potency of multidentate (N4O2) (ethylenediamine)bis[propyl(R-benzylimino)]metal(III) cations" J Med Chem. Aug. 30, 1996;39(18):3483-90.
Sharma, V., et al. "Characterization of a 67Ga/68Ga radiopharmaceutical for SPECT and PET of MDR1 P-glycoprotein transport activity in vivo: validation in multidrug-resistant tumors and at the blood-brain barrier" J Nucl Med. Feb. 2005;46(2):354-64.
Sivapackiam, J., et al. "Targeted chemotherapy in drug-resistant tumors, noninvasive imaging of P-glycoprotein-mediated functional transport in cancer, and emerging role of Pgp in neurodegenerative diseases" Methods Mol Biol. 2010;596:141-81.
Sivapackiam, J., et al. "Synthesis, molecular structure, and validation of metalloprobes for assessment of MDR1 P-glycoprotein-mediated functional transport" Dalton Trans. Jul. 7, 2010;39(25):5842-50. Epub May 27, 2010.
Tsang, B.W., et al. "Structure-distribution relationships for metal-labeled myocardial imaging agents: comparison of a series of cationic gallium (III) complexes with hexadentate bis-(salicylaldimine) ligands" J Med Chem. Dec. 9, 1994;37(25):4400-6.
Tsang, B.W., et al. "A gallium-68 radiopharmaceutical that is retained in myocardium: 68Ga[(4,6-MeO2sal)2BAPEN] +" J Nucl Med. Jul. 1993;34(7):1127-31
Yang, B.Y., Jeong JM, Kim YJ, Choi JY, Lee YS, Lee DS, Chung JK, Lee MC. Formulation of 68Ga BAPEN kit for myocardial positron emission tomography imaging and biodistribution study. Nucl Med Biol. Feb. 2010;37(2):149-55. Epub Nov. 26, 2009.
Ziegler, J., et al. "The propionate of heme binds N4O2 Schiff base antimalarial drug complexes" Inorg Chem. Aug. 7, 2000;39(16):3731-3.

* cited by examiner

PET/SPECT AGENTS FOR APPLICATIONS IN BIOMEDICAL IMAGING

CROSS-REFERENCE TO RELATED APPLICATIONS

The present application is a National Stage entry application of and claims the benefit of PCT/US12/024752 international filing date 10 Feb. 2012 and claims the benefit of U.S. Provisional Patent Application Ser. No. 61/441,732 filed 11 Feb. 2011. These applications are incorporated by reference, each in its entirety.

STATEMENT OF GOVERNMENT SUPPORT

This invention was made with government support under AG033328 and CA94056 awarded by the National Institutes of Health. The government has certain rights in the invention.

TECHNICAL FIELD

The present disclosure is in the field of ligands and radioisotopic tracers that can be useful as imaging agents for in vivo positron emission tomography (PET) or single photon emission computed tomography (SPECT) imaging of tissues such as heart or tumors.

BACKGROUND

Coronary heart disease (CHD) is a leading cause of death in the United States. Annual costs of approximately $475 billion have been estimated by the NIH for heart and stroke diseases. Myocardial perfusion scintigraphy is widely employed in the evaluation of patients with known or suspected coronary artery disease (CAD) and myocardial perfusion imaging (MPI) has acquired great value in nuclear cardiology. While $^{99m}$Tc-Sestamibi and $^{201}$Tl, both single photon agents, have dominated the MPI field for the past two decades, there has been great interest in the development of Positron Emission Tomography (PET) perfusion agents to exploit the potential for enhanced spatial and dynamic resolution that PET offers. However, no $^{18}$F-based agent is yet clinically available. Interestingly, there has been a recent increase in world-wide intensity for developing $^{68}$Ga-based radiopharmaceuticals as potential new PET agents, which may provide a non-cyclotron-based resource for new PET radiopharmaceuticals and applications. In addition, recent threats to the stable production and supply chain of $^{99m}$Tc have added further urgency to the search for a viable PET perfusion agent. Among the several agents that are commercially available for perfusion imaging, all of these suffer from one or more shortcomings that render them less than ideal for cardiac perfusion studies. Among these shortcomings are: a) limited first pass extraction at high flow ($^{99m}$Tc-Sestamibi and Thallous Chloride Tl-201) and b) poor liver clearance ($^{99m}$-Sestamibi, $^{99m}$Tc-teboroxime. $^{99m}$Tc-Tetrofosmin, and $^{99m}$Tc-Q complexes). While the former factor can decrease sensitivity, the latter component can increase background noise from adjacent tissues thereby afficting signal-to-noise ratios. The resulting image quality can be less than optimal for interpretation by clinicians in nuclear medicine or physicians such as radiologists.

Positron Emission Tomography (PET) technology allows a three dimensional reconstruction of the distribution of radiopharmaceuticals in vivo to quantify tissue activity levels and allow high resolution imaging. Ga-68 is considered a short-lived positron emitting radionuclide available from $^{68}$Ge/$^{68}$Ga generator systems. These systems are widely available in Europe and are employed for clinical applications across the continent. Such generator systems can be installed in any small nuclear medicine facility nationwide and are not dependent on cyclotrons to produce PET radionuclides. Furthermore, there are two gallium radioisotopes: Ga-68 and Ga-67. The other radionuclide, Gallium-67 can be produced from a cyclotron from Zinc-68 and has a half-life of 78.2 hours, and is commercially available as radioactive gallium chloride or gallium citrate for single photon emission computed tomography (SPECT) applications.

The multidrug resistance (MDR1) P-glycoprotein (Pgp; ABCB1) is an outwardly directed membrane transporter expressed on the cell surface of many normal tissues as well as multidrug resistance cancers. Because Pgp is also expressed on the biliary surface of hepatocytes, the transporter functions to excrete substances into the bile. Thus, MPI agents that are recognized by Pgp, such as $^{99m}$Tc-sestambi, show rapid clearance profiles from the liver, which significantly reduces cross-contamination of liver signals into the inferior wall of the myocardium. This important property results in more reliable and enhanced quantitative analysis of myocardial images in nuclear medicine clinics.

Pgp is also localized on the luminal surface of vascular endothelial cells of the brain and serves as a component of the blood-brain barrier (BBB). Acting as an efflux transporter, Pgp is believed to block brain uptake of moderately hydrophobic drugs by directly excluding such substances from the CNS compartment, thereby offering a natural protection mechanism for the brain. Apart from the well-characterized role of Pgp as a mediator of chemotherapeutic multidrug resistance in cancer patients, Pgp has also been postulated to play an important role in development of Aβ-pathophysiology within the brain, as well as in other neurodegenerative disorders. Additionally, many agents recognized by Pgp are moderately hydrophobic as well as cationic under physiological conditions; some hydrophobic cations are known to penetrate Pgp negative cells or tissues in response to negative transmembrane potentials (both plasma- and mitochondrial potentials), and are localized within the mitochondria. Among various tissues, myocardium is mitochondrial rich and is also a Pgp negative tissue.

WO2008/128058 of H. Kung discloses a compound of formula

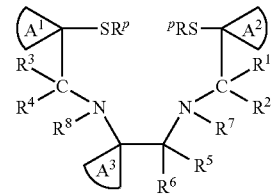

or a pharmaceutically acceptable salt thereof, wherein $A^1$, $A^2$ and $A^3$ are the same or different cycloalkyl, wherein at least one of $A^1$, $A^2$ or $A^3$ is substituted; $R^1$, $R^2$, $R^3$, $R^4$, $R^5$, and $R^6$ are independently hydrogen or alkyl; $R^7$ and $R^8$ are independently hydrogen or alkyl, and $R^P$ is hydrogen or a sulthydryl protecting group.

SUMMARY OF INVENTION

The present inventors have realized that MPI probes are needed that optimally have a combination of the following characteristics: a) enhanced first pass extraction into heart tissue compared to presently available probes, b) linearity with true blood flow, c) enhanced detection of myocardial viability compared to presently available probes, d) reduced liver retention compared to presently available probes, and e) more efficient clearance from non cardiac and adjoining tissues compared to presently available probes. Additionally, for a probe requiring the incorporation of a radionuclide, it would be advantageous if production of the radionuclide were not limited by proximity to a cyclotron or to a sophisticated radiochemistry laboratory.

In view of these needs, the present inventors have developed a series of tracers. The present teachings include compounds, chelates, complexes, and salts. In various embodiments, the compounds, chelates, complexes, and salts of the present teachings can be used as probes in positron emission tomography (PET scanning) and single photon emission computed tomography (SPECT imaging) in myocardial perfusion imaging. In various configurations, a tracer of the present teachings can be beneficial in myocardial perfusion imaging to evaluate the regional blood flow in the myocardium, monitor function of the blood-brain barrier in neurodegenerative diseases, probe diseases associated with mitochondrial disfunction as well as apoptosis, and image drug-resistant tumors in cancer chemotherapy to stratify patients likely to benefit from a given chemotherapeutic treatment.

The present inventors have developed a gallium(III) agent

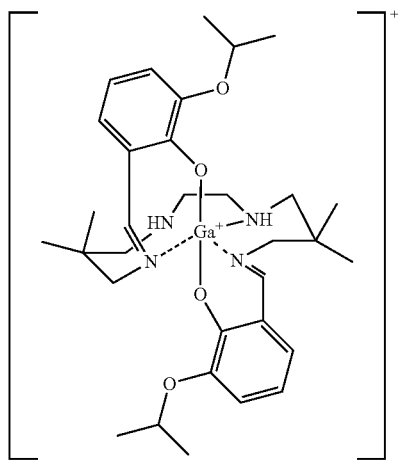

1 incorporating an organic scaffold possessing six donor atoms

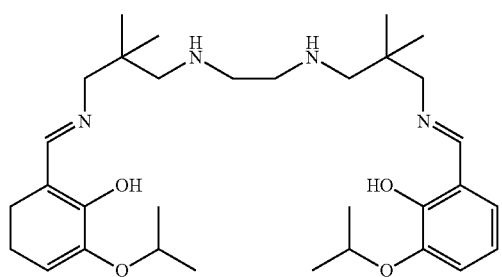

2 resulting in an octahedral geometry. The crystal structure of 1 showed a symmetrical engagement of the four nitrogen atoms in the equatorial plane and two axial phenolate atoms (FIG. 1). Following chemical characterization using routine analytical tools such as $^1$H NMR, proton-decoupled $^{13}$C NMR, and HRMS analysis, the agent could be validated via multiple bioassays in cellulo and in vivo. A $^{67}$Ga-labeled counterpart (1A) has been synthesized, characterized via HPLC (FIG. 2), and evaluated via cell transport studies and quantitative biodistribution studies in mdr1a/1b$^{(-/-)}$ gene-deleted mice and their wild-type (WT) counterparts. In some investigations, the radiolabeled $^{67}$Ga-analogue showed high accumulation in human epidermal carcinoma drug-sensitive KB-3-1 cells (–Pgp), human breast carcinoma MCF-7 (–Pgp) cells and low accumulation in MDR KB-8-5 (+Pgp), KB-8-5-11 (++Pgp) cells, including the stably transfected MCF-7/MDR1 (+Pgp) cells. LY335979 (1 μM), an inhibitor of Pgp, enhanced accumulation in multidrug resistant (MDR, +Pgp) KB-8-5, KB-8-5-11 cells, and stably transfected MCF-7/MDR1 cells, thus demonstrating its responsiveness to Pgp-mediated functional transport activity in cellulo (FIG. 3). In mdr1a/1b$^{(-/-)}$ gene-deleted mice, the $^{67}$Ga-metalloprobe showed 16-fold greater brain penetration and retention (% ID/g=0.96) compared with WT counterparts (% ID/g=0.06), 2 h post injection of the agent 1A (Table 1 and Table 2). Additionally, 1A also showed 2.6 fold higher retention in blood of mdr1a/1b$^{(-/-)}$ gene-deleted mice compared with WT counterparts (Table 1 and Table 2), consistent with Pgp expression in white cells of WT mice. These data indicate the ability of 1A to be transported by Pgp and to serve as a probe of the Pgp-mediated BBB.

An ideal myocardial imaging agent should show high concentration of the radiotracer in the myocardium relative to blood levels and relative to its concentration in the non-targeted tissues. Therefore, design characteristics for heart imaging can include: a) high myocardial tissue uptake, high heart/blood ratios for superior signal-to-noise, and prolonged retention in the myocardium relative to blood and other adjacent tissues in the thoracic cavity. In some configurations, agent

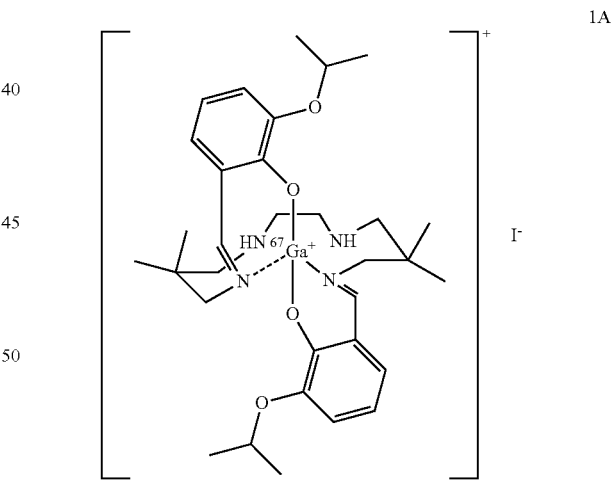

1A can permeate heart tissue, accompanied by a rapid clearance from the livers of mice (Table 1 and Table 2) and rats (Table 3), thus leading to high target-to-background ratios. In various aspects, these features can fulfill critical characteristics of an ideal probe for perfusion imaging. Furthermore, in some investigations, heart/blood and heart/liver ratios in rats tissues (Table 4) were found to be 138 and 8, respectively, at 120 min post injection (P.I.) These target-to-background ratios were 10.4 times (heart/blood) and 10.8 times (heart/liver) greater than ratios reported for gallium-bisaminothiolate complexes for myocardial perfusion imaging in PCT application publication WO2008/128058 A1 of Kung. Additionally, in various configurations, synthesis, purification, and formulation of the agent can be accomplished in less than 60 minutes.

In some embodiments, the inventors' strategy can also include incorporation of Ga-68, a generator-produced radionuclide, into the scaffold. The present teachings also include agent

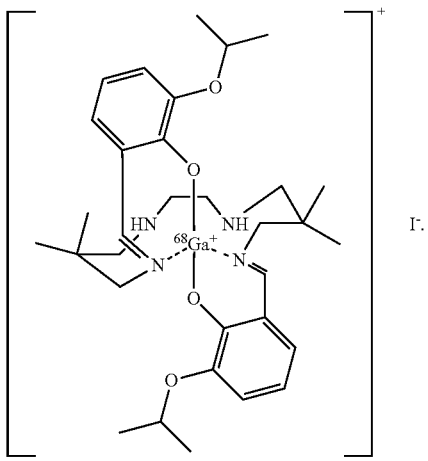

In addition, the inventors disclose kits comprising a ligand of the present teachings. In various configurations, a kit can be used for distribution and/or on-site synthesis of a radiopharmaceutical agent such as 1A and/or 1B.

In various embodiments, the present teachings provide a platform technology for development of PET or SPECT myocardial perfusion imaging agents such as 1A and 1B.

In various embodiments, the present teachings include disclosure of synthesis schemes for some agents of the present teachings.

In various configurations, probes of the present teachings, such as $^{67}$Ga and $^{68}$Ga-metalloprobes, can also enable noninvasive monitoring of the blood-brain barrier in neurodegenerative diseases, probe disease processes associated with disfunction of mitochondrial potential, and assessment of tumors to stratify patient populations for chemotherapeutic treatments.

The present inventors have developed organic compounds, including chelates, complexes and salts thereof comprising a compound of structure

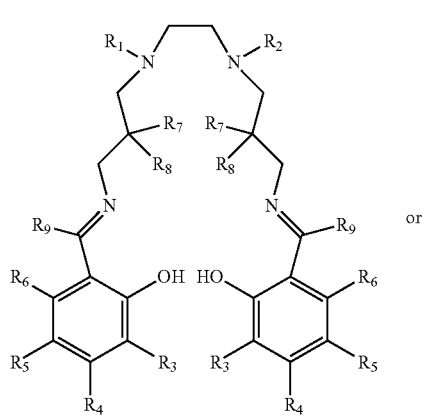

or

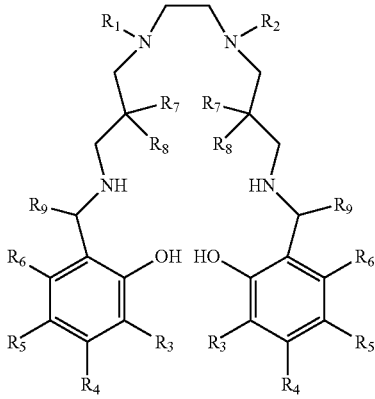

wherein $R_1$, $R_2$, $R_7$ and $R_8$ can each be independently selected from the group consisting of H, $C_1$-$C_6$ linear alkyl, $C_3$-$C_6$ branched chain alkyl, $C_3$-$C_6$ cycloalkyl, $C_1$-$C_4$ linear alkoxy, $C_3$-$C_6$ branched chain alkoxy and $C_3$-$C_6$ cycloalkoxy; $R_3$, $R_4$, $R_5$ and $R_6$ can each be independently selected from the group consisting of H, $C_1$-$C_6$ linear alkoxy, $C_3$-$C_6$ branched chain alkoxy, $C_3$-$C_6$ cycloalkoxy, $C_1$-$C_6$ linear haloalkoxy, $C_3$-$C_6$ branched chain haloalkoxy, $C_3$-$C_6$ cyclohaloalkoxy, $C_1$-$C_6$ linear hydroxyalkoxy, $C_3$-$C_6$ branched chain hydroxyalkoxy, $C_3$-$C_6$ cyclohydroxyalkoxy, alkoxymethyl, alkoxyethyl, alkoxyalkoxymethyl, alkoxyalkoxyethyl, benzyl, alkoxybenzyl, napthyl and alkoxynaphthyl; and $R_9$ can be selected from the group consisting of H, methylene (with reduced Schiff-base as shown, II), carbonyl (as an amide linkage), sulfur, $C_1$-$C_5$ linear alkyl, $C_3$-$C_8$ branched chain alkyl, $C_3$-$C_5$ cycloalkyl, $C_1$-$C_5$ linear alkoxy, $C_3$-$C_8$ branched chain alkoxy and $C_3$-$C_5$ cycloalkoxy, with a proviso that at least one of $R_3$, $R_4$, $R_5$ and $R_6$ is not H.

In some configurations, $R_1$ and $R_2$ can each be independently selected from the group consisting of H, $C_1$-$C_6$ linear alkyl, $C_3$-$C_6$ branched chain alkyl and $C_3$-$C_6$ cycloalkyl.

In some configurations, $R_7$ and $R_8$ can each be independently selected from the group consisting of H, $C_1$-$C_6$ linear alkyl and $C_3$-$C_6$ branched chain alkyl.

In some configurations, $R_3$, $R_4$, $R_5$ and $R_6$ can each be independently selected from the group consisting of $C_1$-$C_6$ linear alkoxy, $C_3$-$C_6$ branched chain alkoxy, $C_3$-$C_6$ cycloalkoxy, alkoxyalkoxyethyl, $C_1$-$C_6$ linear haloalkoxy, $C_3$-$C_6$ branched chain haloalkoxy, $C_3$-$C_6$ cyclohaloalkoxy, $C_1$-$C_6$ linear hydroxyalkoxy, $C_3$-$C_6$ branched chain hydroxyalkoxy, $C_3$-$C_6$ cyclohydmrxyalkoxy, benzyl, and naphthyl.

In some configurations, $R_3$, $R_4$, $R_5$ and $R_6$ can each be independently selected from the group consisting of $C_1$-$C_6$ linear alkoxy, $C_3$-$C_6$ branched chain alkoxy, $C_3$-$C_6$ cycloalkoxy, alkoxyalkoxyethyl, $C_1$-$C_6$ linear haloalkoxy, $C_3$-$C_6$ branched chain haloalkoxy, $C_3$-$C_6$ cyclohaloalkoxy, $C_1$-$C_6$ linear hydroxyalkoxy, $C_3$-$C_6$ branched chain hydroxyalkoxy, $C_3$-$C_8$ cyclohydroxyalkoxy, alkoxybenzyl, and alkoxynaphthyl.

In some configurations, $R_3$, $R_4$, $R_5$ and $R_6$ can each be independently selected from the group consisting of $C_1$-$C_6$ linear alkoxy, $C_3$-$C_6$ branched chain alkoxy, alkoxyalkoxyethyl, $C_1$-$C_6$ linear haloalkoxy, $C_3$-$C_6$ branched chain haloalkoxy, $C_1$-$C_6$ linear hydroxyalkoxy and $C_3$-$C_6$ branched chain hydroxyalkoxy.

In some aspects, an alkoxybenzyl of at least one of $R_3$, $R_4$, $R_5$ and $R_6$ can be an ortho-, a meta-, or a para-methoxybenzyl moiety.

In some configurations, $R_3$, $R_4$, $R_5$ and $R_6$ can each be independently selected from the group consisting of H, $C_3$-$C_6$ linear alkoxy, $C_3$-$C_6$ branched chain alkoxy and $C_3$-$C_6$ cycloalkoxy.

In some configurations, $R_3$, $R_4$, $R_5$ and $R_6$ can each be independently selected from the group consisting of H and $C_3$-$C_6$ branched chain alkoxy.

In some configurations, $R_3$, $R_4$, $R_5$ and $R_6$ can each be independently selected from the group consisting of H and isopropoxy.

In some configurations, $R_3$ and $R_5$ can each be isopropoxy and $R_4$ and $R_6$ can be H.

In some configurations, $R_4$ and $R_6$ can each be isopropoxy and $R_3$ and $R_5$ can each be H.

In some configurations $R_3$, $R_4$, $R_5$ and $R_6$ can each be isopropoxy or H, wherein at least two of $R_3$, $R_4$, $R_5$ and $R_6$ are isopropoxy and at least one of $R_3$, $R_4$, $R_5$ and $R_6$ is H.

In some configurations, $R_4$, $R_4$, $R_5$ and $R_6$ can each be isopropoxy or H, wherein at least three of $R_3$, $R_4$, $R_5$ and $R_6$ are isopropoxy and at least one of $R_3$, $R_4$, $R_5$ and $R_6$ is H.

In some configurations, $R_1$ and $R_2$ can each be independently selected from the group consisting of H and methyl.

In some configurations, $R_7$ and $R_8$ can each be methyl.

In some configurations, $R_3$, $R_4$, $R_5$ and $R_6$ can each be independently selected from the group consisting of H, $C_1$-$C_6$ linear alkoxy, $C_3$-$C_6$ branched chain alkoxy, $C_3$-$C_6$ cycloalkoxy, $C_1$-$C_6$ linear haloalkoxy, $C_3$-$C_6$ branched chain haloalkoxy, $C_3$-$C_6$ cyclohaloalkoxy, $C_1$-$C_6$ linear hydroxyalkoxy, $C_3$-$C_6$ branched chain hydroxyalkoxy, $C_3$-$C_6$ cyclohydroxyalkoxy, alkoxybenzyl, napthyl and alkoxynaphthyl.

In some configurations, $R_4$, $R_5$ and $R_6$ can each be H, and $R_3$ can be selected from the group consisting of $C_1$-$C_6$ linear alkoxy, $C_3$-$C_6$ branched chain alkoxy, $C_3$-$C_6$ cycloalkoxy, $CH(CH_2)$ linear haloalkoxy, n=0 to 5, $C_3$-$C_6$ branched chain haloalkoxy. $C_3$-$C_6$ cyclohaloalkoxy, $C_1$-$C_6$ linear hydroxyalkoxy, $C_3$-$C_6$ branched chain hydroxyalkoxy. $C_3$-$C_8$ cyclohydroxyalkoxy, $C_1$-$C_6$ alkoxybenzyl, napthyl and $C_1$-$C_6$ alkoxynaphthyl.

In some configurations, $R_4$, $R_5$ and $R_6$ can each be H, and $R_3$ can be selected from the group consisting of $C_1$-$C_6$ linear alkoxy, $C_3$-$C_6$ branched chain alkoxy and $C_3$-$C_6$ cycloalkoxy.

In some configurations, $R_4$, $R_5$ and $R_6$ can each be H, and $R_3$ can be selected from the group consisting of $C_1$-$C_6$ linear alkoxy and $C_3$-$C_6$ branched chain alkoxy.

In some configurations, $R_4$, $R_5$ and $R_6$ can each be H, and $R_3$ can be a $C_3$-$C_6$ branched chain alkoxy.

In some configurations, $R_4$, $R_5$ and $R_6$ can each be H, and $R_3$ can be an isopropoxy moiety.

In some configurations, $R_3$, $R_4$, $R_5$ and $R_6$ can each be independently selected from the group consisting of methoxymethyl, methoxyethoxyethyl, p-methoxybenzyl, benzyl, naphthyl, and $CH_3(CH_2)_n$-alkoxynaphthyl, n=0 to 5.

In some configurations, an organic scaffold comprising six donor atoms can result in an octahedral geometry. In various configurations, a haloalkoxy of the present teachings can be a bromoalkoxy, a fluoroalkoxy, a chloroalkoxy, or a iodoalkoxy. In various configurations, an organic molecule of the present teachings can serve as a chelate, and can form a complex with a metal cation, such as, without limitation, gallium. In some configurations, the metal cation can be a radionuclide such as, without limitation, a $^{67}Ga$ or a $^{68}Ga$. For example, the present teachings include, without limitation.

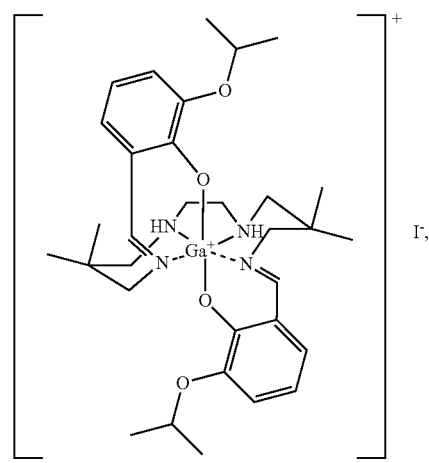

1

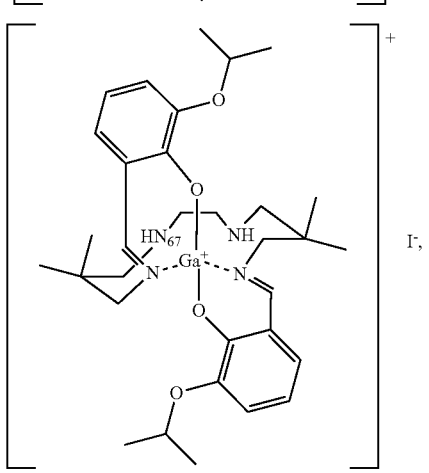

1A

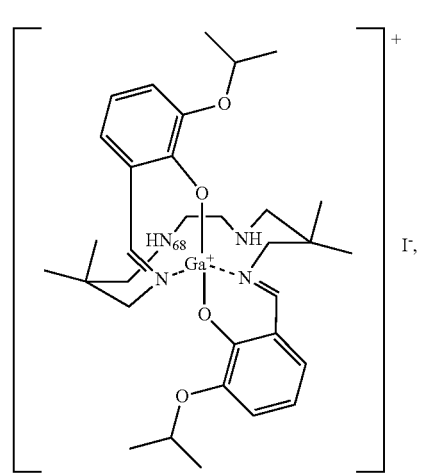

1B

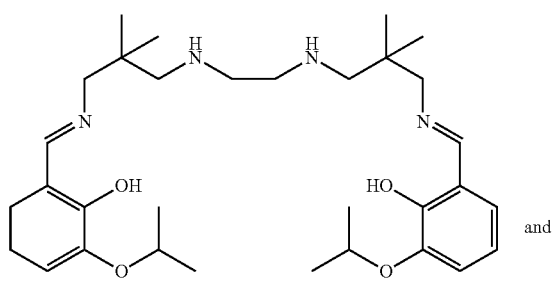

2 and

-continued

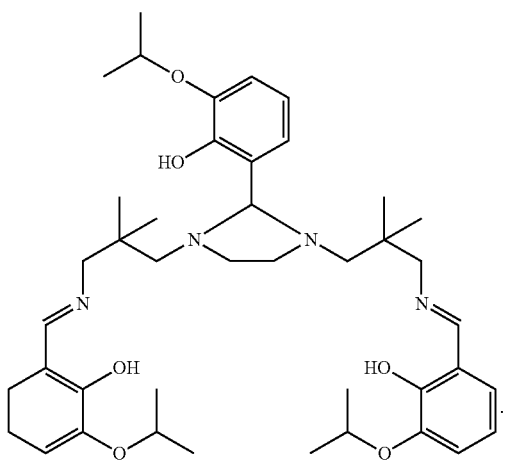

Aspects

The present teachings include the following aspects.

1. A compound, chelate, complex or salt thereof comprising a structure selected from the group consisting of

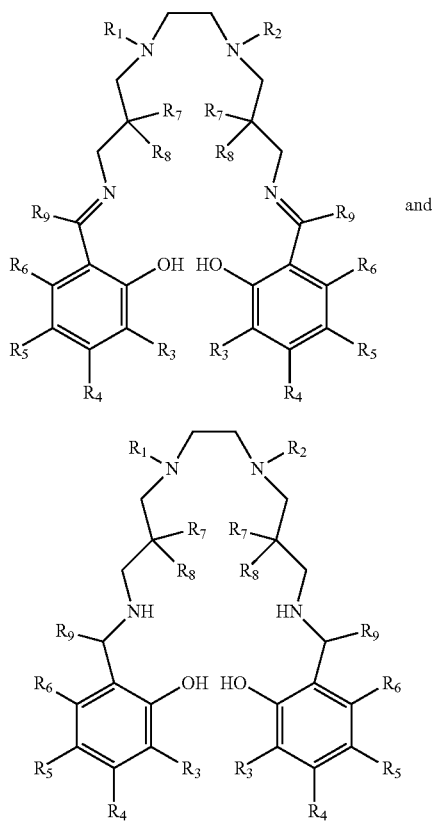

wherein $R_1$, $R_2$, $R_7$ and $R_8$ can each be independently selected from the group consisting of H, $C_1$-$C_6$ linear alkyl, $C_3$-$C_6$ branched chain alkyl, $C_3$-$C_6$ cycloalkyl, $C_1$-$C_6$ linear alkoxy, $C_3$-$C_6$ branched chain alkoxy and $C_3$-$C_6$ cycloalkoxy; $R_3$, $R_4$, $R_5$ and $R_6$ can each be independently selected from the group consisting of H, $C_1$-$C_6$ linear alkoxy, $C_3$-$C_6$ branched chain alkoxy, $C_3$-$C_6$ cycloalkoxy, $C_1$-$C_6$ linear haloalkoxy, $C_3$-$C_6$ branched chain haloalkoxy, $C_3$-$C_6$ cyclohaloalkoxy, $C_1$-$C_6$ linear hydroxyalkoxy, $C_3$-$C_6$ branched chain hydroxyalkoxy, $C_3$-$C_6$ cyclohydroxyalkoxy, alkoxymethyl, alkoxyethyl, alkoxyalkoxymethyl, alkoxyalkoxyethyl, benzyl, alkoxybenzyl, napthyl and alkoxynaphthyl; and $R_9$ can be selected from the group consisting of H, methylene (with reduced Schiff-base as shown, II), carbonyl (as an amide linkage), sulfur, $C_1$-$C_5$ linear alkyl, $C_3$-$C_5$ branched chain alkyl, $C_3$-$C_5$ cycloalkyl, $C_1$-$C_8$ linear alkoxy, $C_3$-$C_8$ branched chain alkoxy and $C_3$-$C_5$ cycloalkoxy, with a proviso that at least one of $R_3$, $R_4$, $R_5$ and $R_6$ is not H.

2. A compound, chelate, complex or salt thereof in accordance with aspect 1, wherein $R_1$ and $R_2$ can each be independently selected from the group consisting of H, $C_1$-$C_6$ linear alkyl, $C_3$-$C_6$ branched chain alkyl and $C_3$-$C_6$ cycloalkyl.

3. A compound, chelate, complex or salt thereof in accordance with aspect 1, wherein $R_7$ and $R_8$ can each be independently selected from the group consisting of H, $C_1$-$C_6$ linear alkyl and $C_3$-$C_6$ branched chain alkyl.

4. A compound, chelate, complex or salt thereof in accordance with aspect 1, wherein $R_3$, $R_4$, $R_5$ and $R_6$ can each be independently selected from the group consisting of $C_1$-$C_6$ linear alkoxy, $C_3$-$C_6$ branched chain alkoxy, $C_3$-$C_6$ cycloalkoxy, alkoxyalkoxyethyl, $C_1$-$C_6$ linear fluoroalkoxy, $C_3$-$C_6$ branched chain haloalkoxy, $C_3$-$C_6$ cyclohaloalkoxy, $C_1$-$C_6$ linear hydroxyalkoxy, $C_3$-$C_6$ branched chain hydroxyalkoxy, $C_3$-$C_6$ cyclohydroxyalkoxy, benzyl, and naphthyl.

5. A compound, chelate, complex or salt thereof in accordance with aspect 1, wherein $R_3$, $R_4$, $R_3$ and $R_6$ can each be independently selected from the group consisting of $C_1$-$C_6$ linear alkoxy, $C_3$-$C_6$ branched chain alkoxy, $C_3$-$C_6$ cycloalkoxy, alkoxyalkoxyethyl, $C_1$-$C_6$ linear haloalkoxy, $C_3$-$C_6$ branched chain haloalkoxy, $C_3$-$C_6$ cyclohaloalkoxy, $C_1$-$C_6$ linear hydroxyalkoxy, $C_3$-$C_6$ branched chain hydroxyalkoxy, $C_3$-$C_6$ cyclohydroxyalkoxy, alkoxybenzyl, and alkoxynaphthyl.

6. A compound, chelate, complex or salt thereof in accordance with aspect 1, wherein $R_3$, $R_4$, $R_5$ and $R_6$ can each be independently selected from the group consisting of $C_1$-$C_6$ linear alkoxy, $C_1$-$C_6$ branched chain alkoxy, alkoxyalkoxyethyl, $C_1$-$C_6$ linear haloalkoxy, $C_3$-$C_6$ branched chain haloalkoxy, $C_1$-$C_6$ linear hydroxyalkoxy and $C_3$-$C_6$ branched chain hydroxyalkoxy.

7. A compound, chelate, complex or salt thereof in accordance with aspect 1, wherein an alkoxybenzyl of at least one of $R_3$, $R_4$, $R_5$ and $R_6$ can be an ortho-, meta-, and para-methoxybenzyl.

8. A compound, chelate, complex or salt thereof in accordance with aspect 1, wherein $R_3$, $R_4$, $R_5$ and $R_6$ can each be independently selected from the group consisting of 1, $C_1$-$C_6$ linear alkoxy, $C_3$-$C_6$ branched chain alkoxy and $C_3$-$C_6$ cycloalkoxy.

9. A compound, chelate, complex or salt thereof in accordance with aspect 1, wherein $R_3$, $R_4$, $R_5$ and $R_6$ can each be independently selected from the group consisting of H and $C_3$-$C_6$ branched chain alkoxy.

10. A compound, chelate, complex or salt thereof in accordance with aspect 1, wherein $R_3$, $R_4$, $R_5$ and $R_6$ can each be independently selected from the group consisting of H and isopropoxy.

11. A compound, chelate, complex or salt thereof in accordance with aspect 1, wherein $R_1$ and $R_2$ can each be independently selected from the group consisting of H and methyl.

12. A compound, chelate, complex or salt thereof in accordance with aspect 11, wherein $R_7$ and $R_5$ can each be a methyl.

13. A compound, chelate, complex or salt thereof in accordance with aspect 12, wherein $R_3$, $R_4$, $R_5$ and $R_6$ can each be independently selected from the group consisting of H, $C_1$-$C_6$ linear alkoxy, $C_3$-$C_6$ branched chain alkoxy, $C_3$-$C_6$ cycloalkoxy. $C_1$-$C_6$ linear haloalkoxy, $C_3$-$C_6$ branched chain haloalkoxy, $C_3$-$C_6$ cyclohaloalkoxy, $C_1$-$C_6$ linear hydroxyalkoxy, $C_3$-$C_6$ branched chain hydroxyalkoxy. $C_3$-$C_6$ cyclohydroxyalkoxy, alkoxybenzyl, napthyl and $C_1$-$C_6$ alkoxynaphthyl.

14. A compound, chelate, complex or salt thereof in accordance with aspect 12, wherein $R_4$, $R_5$ and $R_6$ can each be H, and $R_3$ can be selected from the group consisting of $C_1$-$C_6$ linear alkoxy. $C_3$-$C_6$ branched chain alkoxy. $C_3$-$C_6$ cycloalkoxy, $C_1$-$C_6$ linear haloalkoxy, $C_3$-$C_6$ branched chain haloalkoxy, $C_3$-$C_6$ cyclohaloalkoxy, $C_1$-$C_6$ linear hydroxyalkoxy, $C_3$-$C_6$ branched chain hydroxyalkoxy, $C_3$-$C_6$ cyclohydroxyalkoxy, alkoxybenzyl, napthyl and $C_1$-$C_6$ alkoxynaphthyl.

15. A compound, chelate, complex or salt thereof in accordance with aspect 12, wherein $R_4$, $R_5$ and $R_6$ can each be H, and $R_3$ can be selected from the group consisting of $C_1$-$C_6$ linear alkoxy, $C_3$-$C_6$ branched chain alkoxy and $C_3$-$C_6$ cycloalkoxy.

16. A compound, chelate, complex or salt thereof in accordance with aspect 12, wherein $R_4$, $R_5$ and $R_6$ can each be H, and $R_3$ can be selected from the group consisting of $C_1$-$C_6$ linear alkoxy and $C_3$-$C_6$ branched chain alkoxy.

17. A compound, chelate, complex or salt thereof in accordance with aspect 12, wherein $R_4$, $R_5$ and $R_6$ can each be H, and $R_3$ can be a $C_3$-$C_6$ branched chain alkoxy.

18. A compound, chelate, complex or salt thereof in accordance with aspect 12, wherein $R_4$, $R_5$ and $R_6$ can each be H, and $R_3$ can be a isopropoxy.

19. A compound, chelate, complex or salt thereof in accordance with aspect 12, wherein $R_3$, $R_4$, $R_5$ and $R_6$ can each be independently selected from the group consisting of methoxymethyl, methoxyethoxyethyl, p-methoxybenzyl, benzyl, naphthyl, and $C_1$-$C_6$ alkoxynaphthyl.

20. A compound, chelate, complex or salt thereof in accordance with aspect 1, wherein $R_7$ and $R_8$ can each be independently selected from the group consisting of $C_1$-$C_6$ linear alkyl. $C_3$-$C_6$ branched chain alkyl, $C_1$-$C_6$ linear alkoxy and $C_3$-$C_6$ branched chain alkoxy.

21. A compound, chelate, complex or salt thereof in accordance with aspect 1, wherein $R_9$ can be selected from the group consisting of H, $C_1$-$C_5$ linear alkyl, $C_3$-$C_5$ branched chain alkyl and $C_3$-$C_5$ cycloalkyl.

22. A compound, chelate, complex or salt thereof in accordance with aspect 1, wherein $R_9$ can be selected from the group consisting of $C_1$-$C_6$ linear alkoxy and $C_3$-$C_6$ branched chain alkoxy.

23. A complex comprising a chelate of any one of aspects 1-22; and a metal ion.

24. A complex in accordance with aspect 23, wherein the metal ion has a six-coordinate ionic radius between 0.50-0.85 Å.

25. A complex in accordance with aspect 23, wherein the metal ion can be selected from the group consisting of a gallium ion, a cobalt ion, an indium ion, an iron ion, thallium ion, a rhenium ion, a rhodium ion, a rubidium ion, a ruthenium ion, a strontium ion, a technetium ion, a tungsten ion, a vanadium ion, an yttrium ion a zirconium ion, and a lanthanide or transition metal trivalent ion.

26. A complex in accordance with aspect 23, wherein the metal ion can be a radionuclide.

27. A complex in accordance with aspect 23, wherein the metal ion can be a positron emitter.

28. A complex in accordance with aspect 23, wherein the metal ion can be a gamma emitter.

29. A complex in accordance with aspect 23, wherein the metal ion can be selected from the group consisting of an ion of gallium-67, an ion of gallium-68, an ion of cobalt-57, an ion of indium-111, an ion of iron-59, an ion of iron-52, an ion of thallium-201, an ion of rhenium-188, an ion of rubidium-82, an ion of strontium-92, an ion of technetium-99m, an ion of yttrium-86, and an ion of zirconium-86.

30. A complex in accordance with aspect 23, wherein the metal ion can be selected from the group consisting of an ion of gallium-67, an ion of gallium-68 and a combination thereof.

31. A complex in accordance with aspect 23, wherein the metal ion can be selected from the group consisting of a gallium ion and an iron ion.

32. A complex in accordance with aspect 31, further comprising a halo-radionuclide 33. A complex in accordance with aspect 32, wherein the halo-radionuclide can be selected from the group consisting of $^{18}$F, $^{75}$Br, $^{76}$Br, $^{123}$I, $^{124}$I, and $^{131}$I and a combination thereof.

34. A salt comprising:
a complex in accordance with any one of aspects 23-31; and an anion.

35. A salt in accordance with aspect 34, wherein the anion can be selected from the group consisting of a halide, a sulfate, a nitrate, a phosphate and an organic anion.

36. A salt in accordance with aspect 34, wherein the anion can be selected from the group consisting of chloride, fluoride, iodide, bromide, phosphate, sulfate, nitrate, sulfonate, perchlorate, tetraphenylborate, hexafluorophosphate and tetrahaloborate.

37. A salt in accordance with aspect 35, wherein the organic anion can be a carboxylate.

38. A salt in accordance with aspect 35, wherein the organic anion can be selected from the group consisting of citrate, carbonate, acetate, malate, maleate, lactate, formate, succinate and oxalate.

39. A salt in accordance with aspect 35, wherein the organic anion can be citrate.

40. A salt in accordance with aspect 35, wherein the anion can be a halide.

41. A salt in accordance with aspect 35, wherein the halide can be selected from the group consisting of a bromide, a fluoride, a chloride and an iodide.

42. A salt in accordance with aspect 34, wherein the metal ion can be a gallium ion.

43. A salt in accordance with aspect 42, wherein the gallium ion can be selected from the group consisting of an ion of gallium-67, an ion of gallium-68 and a combination thereof.

44. A salt in accordance with any one of aspects 34-43, having structure

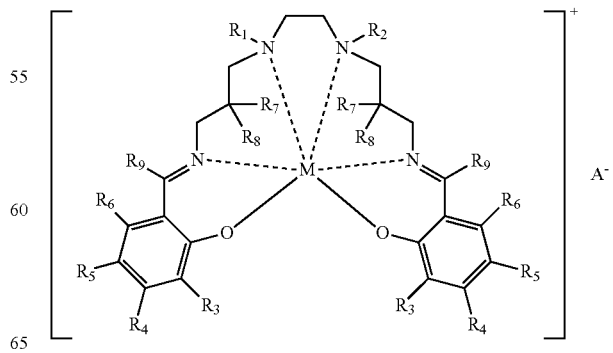

wherein M is a metal ion and A⁻ is an anion.

45. A salt in accordance with aspect 44, selected from the group consisting of

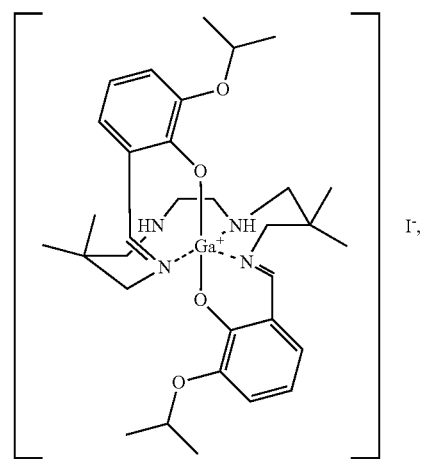

I⁻,

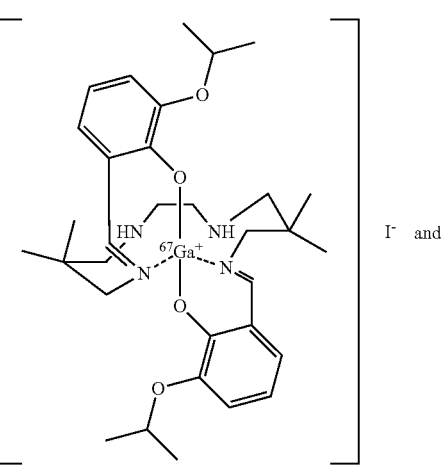

I⁻ and

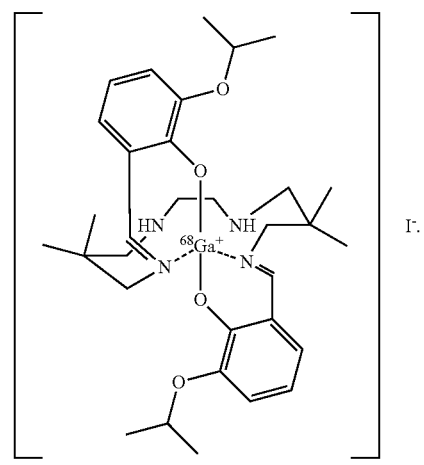

I⁻.

46. A chelate, a complex thereof, or a salt thereof selected from the group consisting of

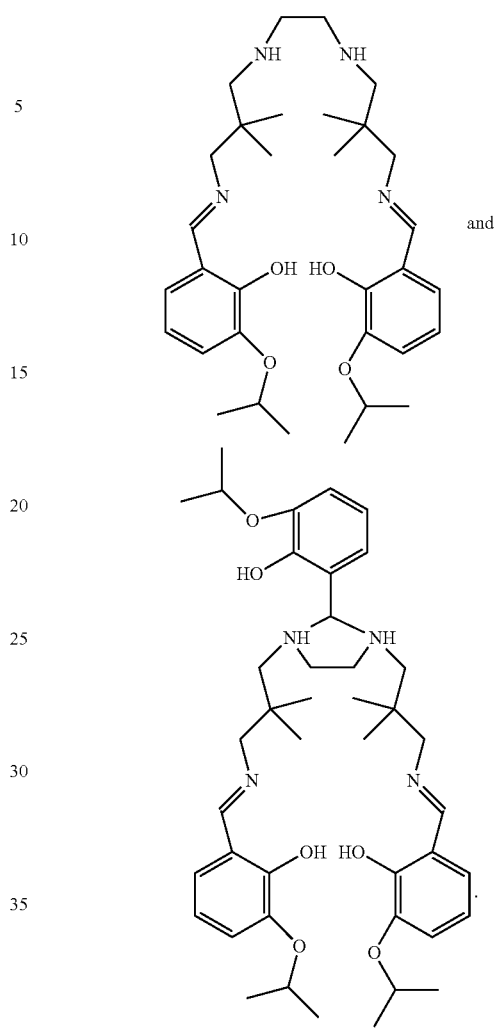

and

47. A method of forming a salt of any one of aspects 34-45, comprising contacting a chelate, a complex thereof or salt thereof of any one of aspects 1-33 with a metal salt.

48. A method of forming a complex in accordance with aspect 47, wherein the metal salt comprises a metal ion selected from the group consisting of a gallium ion, a cobalt ion, an indium ion, an iron ion, a thallium ion, a rhenium ion, a rhodium, a rubidium ion, a ruthenium ion, a strontium ion, a technetium ion, a tungsten ion, a vanadium ion, an yttrium ion, a zirconium ion and a lanthanide or transition metal trivalent ion.

49. A method of forming a complex in accordance with aspect 47, wherein the metal salt comprises an ion of gallium-67, an ion of gallium-68, an ion of cobalt-57, an ion of indium-111, an ion of iron-59, an ion of iron-52, an ion of thallium-201, an ion of rhenium-188, an ion of rubidium-82, an ion of strontium-92, an ion of technetium-99m, an ion of yttrium-86, and an ion of zirconium-86.

50. A method of forming a complex in accordance with aspect 47, wherein the metal salt comprises an ion of gallium-67 or an ion of gallium-68.

51. A kit for forming a complex, comprising:
a compound, chelate, complex or salt of any one of aspects 1-46; and a metal salt comprising a metal ion and an anion.

52. A kit in accordance with aspect 51, wherein the metal ion is selected from the group consisting of a gallium ion, a cobalt ion, an indium ion, an iron ion, thallium ion, a rhenium ion, a rhodium, a rubidium ion, a ruthenium ion, a strontium ion, a technetium ion, a tungsten ion, a vanadium ion, an yttrium ion, a zirconium ion, a lanthanide ion and a transition metal trivalent ion.

53. A kit in accordance with aspect 51, wherein the metal ion is selected from the group consisting of an ion of gallium-67, an ion of gallium-68, an ion of cobalt-57, an ion of indium-111, an ion of iron-59, an ion of iron-52, an ion of thallium-201, an ion of rhenium-188, an ion of rubidium-82, an ion of strontium-92, an ion of technetium-99m, an ion of yttrium-86, and an ion of zirconium-86.

54. A kit in accordance with aspect 51, wherein the metal ion is selected from the group consisting of an ion of gallium-67, an ion of gallium-68, a combination thereof.

55. A kit in accordance with any one of aspects 51-54, further comprising instructions for using the compound to image a region in a subject.

56. A method of imaging Pgp distribution in a region in a subject, comprising the steps:
administering to a subject a complex or salt of any one of aspects 23-46; subjecting a region of interest of the subject to radiation; and subjecting the subject to PET scanning or SPECT scanning.

57. A method of imaging the distribution of MDR1 (multidrug resistance) P-glycoprotein (Pgp; ABCB1) in a mammalian subject, comprising:
administering to the subject a composition comprising a chelate, complex or salt of any one of aspects 1-46: and subjecting the subject to PET imaging, wherein the chelate, complex or salt comprises a positron-emitting isotope.

58. A method in accordance with aspect 57, wherein the positron-emitting isotope is gallium-68.

59. A method of imaging the distribution of MDR1 (Multidrug Resistance) P-glycoprotein (Pgp; ABCB1) in a mammalian subject, comprising:
administering to the subject a composition comprising a chelate, complex or salt of any one of aspects 1-46: and subjecting the subject to SPECT imaging, wherein the chelate, complex or salt comprises a gamma-emitting isotope.

60. A method in accordance with aspect 59, wherein the gamma-emitting isotope is gallium-67.

61. A method in accordance with any one of aspects 56-60, wherein the imaging a region in a subject comprises imaging the distribution of an ATP binding cassette (ABC) transporter.

62. A method in accordance with any one of aspects 56-61, wherein the subject is a human.

63. A method in accordance with any one of aspects 56-62, wherein the imaging the distribution of an ABC transporter comprises imaging liver clearance of the complex or salt.

64. A method in accordance with any one of aspects 56-62, wherein the imaging the distribution of an ABC transporter comprises imaging myocardial retention of the complex or salt.

65. A method of imaging myocardium perfusion, comprising administering a complex or salt of any one of aspects 34-43 to a subject and subjecting the subject to PET, SPECT, or MRI imaging.

66. A method in accordance with any one of aspects 56-62, wherein the imaging distribution of Pgp comprises imaging a tumor.

67. A method in accordance with aspect 66, wherein the imaging a tumor comprises imaging a drug-resistant tumor.

68. A method in accordance with aspect 66, wherein the imaging a tumor comprises imaging a drug-sensitive tumor.

69. A method in accordance with any one of aspects 57-62, wherein the imaging distribution of Pgp comprises imaging the brain of the subject.

70. A method in accordance with aspect 69, wherein the imaging the brain comprises imaging the blood-brain barrier.

71. A method in accordance with any one of the aspects 57-62, wherein the imaging comprises imaging the depolarization of the membrane potential.

72. A method of treating an anemia, comprising administering to a subject in need thereof a pharmaceutical composition comprising a complex or salt thereof of any one of aspects 1-46.

73. A method of treating an anemia in accordance with aspect 72, wherein the complex or salt comprises an iron ion.

74. A fertilizer comprising a compound, a chelate, a complex thereof or a salt thereof in accordance with any one of aspects 1-46.

75. A fertilizer in accordance with aspect 74, wherein the complex or salt comprises an iron ion.

76. A compound of formula

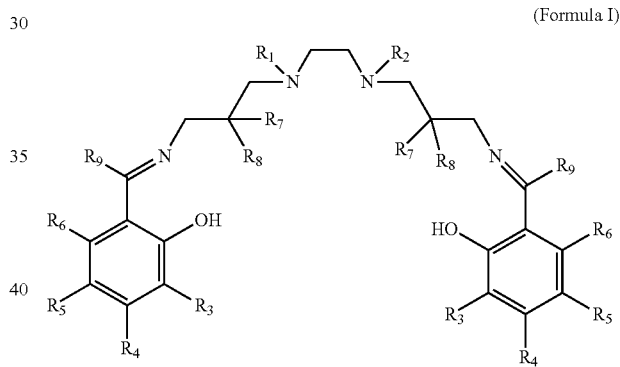

(Formula I)

or a pharmacologically acceptable complex or salt thereof, wherein:

$R_1$ and $R_2$ can each be independently selected from the group consisting of H, methyl, ethyl, straight chain propyl, straight chain butyl, straight chain pentyl straight chain hexyl, branched chain propyl, branched chain butyl, branched chain pentyl and branched chain hexyl;

$R_3$, $R_4$, $R_5$, and $R_6$ can each be independently selected from the group consisting of H, methyl, ethyl, straight chain propyl, branched chain propyl, straight chain butyl, branched chain butyl, straight chain pentyl, branched chain pentyl, straight chain hexyl and branched chain hexyl, methoxy, ethoxy, fluoroalkoxy. $C_1$-$C_6$ hydroxyalkoxy, $C_1$-$C_6$ alkoxyalkoxyethyl, straight chain propoxy, branched chain propoxy, straight chain butoxy, branched chain butoxy, straight chain pentyloxy, branched chain pentyloxy, straight chain hexyloxy and branched chain hexyloxy, methoxymethyl, methoxyethoxy ethyl, p-methoxybenzyl, benzyl, naphthyl and $C_1$-$C_6$ alkoxy substituted naphthyl;

$R_7$, $R_8$ can each be independently selected from the group consisting of H, methyl, ethyl, straight chain propyl, branched chain propyl, butyl, pentyl and hexyl;

$R_9$ can be selected from the group consisting of H, methyl, ethyl, straight chain propyl, and a branched alkyl selected from the group consisting of isopropyl, isobutyl, isopentyl tert-butyl and tert-pentyl, with a proviso that at least one of $R_1$, $R_2$, $R_3$, $R_4$, $R_5$, $R_6$, $R_7$, $R_8$ and $R_9$ is not H.

77. A compound or a pharmacologically acceptable complex or salt thereof in accordance with aspect 76, wherein at least one of $R_3$, $R_4$, $R_5$, and $R_6$ is not H.

78. A compound or a pharmacologically acceptable complex or salt thereof in accordance with aspect 76, wherein $R_3$, $R_4$, $R_5$, and $R_6$ can each be independently selected from the group consisting of branched chain propoxy, branched chain butoxy, branched chain pentyloxy and branched chain hexyloxy.

79. A compound or a pharmacologically acceptable complex or salt thereof in accordance with aspect 76, wherein $R_3$, $R_4$, $R_5$ and $R_6$ can each be independently selected from the group consisting of methoxy, ethoxy, fluoroalkoxy, hydroxyalkoxy, alkoxyalkoxyethyl, straight chain propoxy, straight chain butoxy, straight chain pentyloxy, straight chain hexyloxy branched chain propoxy, branched chain butoxy, branched chain pentlyoxy and branched chain hexyloxy.

80. A compound or a pharmacologically acceptable complex or salt thereof in accordance with aspect 77, wherein $R_3$, $R_4$, $R_5$ and $R_6$ can each independently be branched chain propoxy.

81. A compound or a pharmacologically acceptable complex or salt thereof in accordance with aspect 76, wherein $R_1$ and $R_2$ can each be independently selected from the group consisting of H, branched chain propyl, branched chain butyl, branched chain pentyl and branched chain hexyl.

82. A compound or a pharmacologically acceptable complex or salt thereof in accordance with aspect 76, wherein $R_1$ and $R_2$ can each be independently selected from the group consisting of H, branched chain propyl, branched chain butyl, branched chain pentyl and branched chain hexyl.

83. A compound or a pharmacologically acceptable complex or salt thereof in accordance with aspect 76, wherein $R_1$ and $R_2$ can each be independently selected from the group consisting of H and methyl, $R_7$ can be methyl, $R_8$ can be methyl, R4 can be H, $R_5$ can be H, $R_6$ can be H, $R_3$ can be selected from the group consisting of isopropyloxy, isobutoxyl, isopentyloxy, straight chain hexyloxy and branched chain hexyloxy.

84. A compound or a pharmacologically acceptable complex or salt thereof in accordance with aspect 76, wherein $R_1$ and $R_2$ can each be independently selected from the group consisting of H and methyl, $R_7$ can be methyl, $R_8$ can be methyl, R3, R4, R5, and R6 can each be independently selected from the group consisting of H, methoxymethyl, methoxyethoxyethyl, p-methoxybenzyl, benzyl, naphthyl, and $C_1$-$C_6$ alkoxysubstituted naphthyls.

85. A compound or a pharmacologically acceptable complex or salt thereof in accordance with any one of aspects 76-84, wherein $R_7$ and $R_8$ can each be independently selected from the group consisting of $C_1$-$C_4$ straight chain alkyl, $C_3$-$C_6$ branched chain alkyl, $C_1$-$C_6$ linear alkoxy, and $C_3$-$C_6$ branched chain alkoxy.

86. A compound or a pharmacologically acceptable complex or salt thereof in accordance with any one of aspects 76-85, wherein $R_9$ can be selected from the group consisting of H, $C_1$-$C_6$ straight chain alkyl, $C_3$-$C_6$ branched chain alkyl, $C_1$-$C_6$ straight chain alkoxy, and $C_3$-$C_6$ branched chain alkoxy.

87. A salt of formula

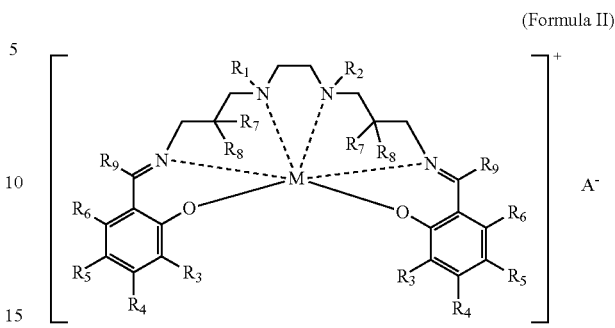

(Formula II)

wherein:

$R_1$ and $R_2$ can each be independently selected from the group consisting of H, methyl, ethyl, straight chain propyl, straight chain butyl, straight chain pentyl straight chain hexyl, branched chain propyl, branched chain butyl, branched chain pentyl and branched chain hexyl;

$R_3$, $R_4$, $R_5$, and $R_6$ can each be independently selected from the group consisting of H, methyl, ethyl, straight chain propyl, branched chain propyl, straight chain butyl, branched chain butyl, straight chain pentyl, branched chain pentyl, straight chain hexyl and branched chain hexyl, methoxy, ethoxy, fluoroalkoxy, hydroxyalkoxy, $C_1$-$C_6$ alkoxyalkoxyethyl, straight chain propoxy, branched chain propoxy, straight chain butoxy, branched chain butoxy, straight chain pentyloxy, branched chain pentyloxy, straight chain hexyloxy and branched chain hexyloxy, methoxymethyl, methoxyethoxy ethyl, p-methoxybenzyl, benzyl, naphthyl and $C_1$-$C_6$ alkoxy substituted naphthyl;

$R_7$, $R_8$ can each be independently selected from the group consisting of H, methyl, ethyl, straight chain propyl, branched chain propyl, butyl, pentyl and hexyl;

$R_9$ can be selected from the group consisting of H, methyl, ethyl, straight chain propyl, and a branched alkyl selected from the group consisting of isopropyl, isobutyl, isopentyl tert-butyl and tert-pentyl;

M can be a metal ion;

$A^-$ can be an anion; with a proviso that at least one of $R_1$, $R_2$, $R_3$, $R_4$, $R_5$, $R_6$, $R_7$, $R_8$ and $R_9$ is not H.

88. A salt in accordance with aspect 87, wherein M can be a metal ion selected from the group consisting of gallium, cobalt, indium, iron, rhenium, rhodium, strontium, tungsten, vanadium, yttribium and zirconium.

89. A salt in accordance with aspect 87, wherein M can be a metal ion selected from the group consisting of gallium, cobalt, indium, iron, rhenium, ruthenium, rhodium, rubidium, strontium, tungsten, vanadium, yttrium, and zirconium.

90. A salt in accordance with aspect 87, wherein $A^-$ can be an anion selected from the group consisting of $Cl^-$, $F^-$, $I^-$, $Br^-$, phosphate, sulfate, nitrate, sulfonate, perchlorate, tetraphenylborate, hexafluorophosphate and tetrafluoroborate.

91. A salt in accordance with aspect 87, wherein at least one of $R_3$, $R_4$, $R_5$, and $R_6$ is not H.

92. A salt in accordance with aspect 91, wherein $R_3$, $R_4$, $R_5$, and $R_6$ can each be independently selected from the group consisting of H, branched chain propoxy, branched chain butoxy, branched chain pentyloxy and branched chain hexyloxy.

93. A salt in accordance with aspect 91, wherein $R_3$, $R_4$, $R_5$ and $R_6$ can each independently be a branched chain propoxy.

94. A salt in accordance with aspect 87, wherein $R_1$ and $R_2$ can each be independently selected from the group consisting of H, branched chain propyl, branched chain butyl, branched chain pentyl and branched chain hexyl.

95. A salt in accordance with aspect 87, wherein $R_1$ and $R_2$ can each be selected from the group consisting of H and a branched chain propyl.

96. A salt in accordance with aspect 87, wherein M can be a radioactive nuclide.

97. A salt in accordance with aspect 87, wherein M can be a radioactive metal ion selected from the group consisting of radioactive gallium-67, gallium-68, cobalt-57, indium-11, iron-59, iron-52, krypton-81, rhenium-188, rubidium-82, strontium-92, technetium-99m, yttrium-86, and zirconium-86.

98. A salt in accordance with aspect 87, wherein M can be gallium-67.

99. A salt in accordance with aspect 87, wherein M can be gallium-68.

100. A salt in accordance with any one of aspects 87-99, wherein M is a metal having a six-coordinate ionic radius between 0.50-0.85 Å.

101. A salt in accordance with any one of aspects 87-100, wherein $A^-$ is selected from the group consisting of a halide, a sulfate, a nitrate, a phosphate and a carboxylate.

102. A salt in accordance with any one of aspects 87-101, wherein M is a gallium and $A^-$ is selected from the group consisting of citrate and chloride.

103. A method of making a salt, comprising mixing a compound of any one of aspects 76-86 with a metal salt.

104. A method of making a salt in accordance with aspect 103, wherein the metal salt is selected from the group consisting of gallium citrate and gallium chloride.

105. A salt made by the method of aspect 103 or aspect 104.

106. A kit for forming a radioactive agent comprising:
a compound of any one of aspects 76-86; and a metal salt comprising a radioactive metal 107. A kit in accordance with aspect 106, further comprising instructions for mixing the compound and the metal salt under conditions that form a radiometric complex suitable for application as an imaging agent.

108. A method of imaging pgp distribution in a subject, comprising: administering to a subject a complex or salt of any one of aspects 1-46 or 76-102; and subjecting the subject to perfusion imaging, wherein the complex or salt comprises a radioactive metal isotope.

109. A method of imaging Pgp distribution in a subject in accordance with aspect 108, wherein the imaging comprises PET scanning.

110. A method of imaging Pgp distribution in a subject in accordance with aspect 108, wherein the imaging comprises SPECT imaging.

111. A method of imaging Pgp distribution in a subject in accordance with aspect 108, further comprising imaging perfusion defects in the heart of the subject.

112. A method of imaging Pgp distribution in a subject in accordance with any one of aspects 108-111, wherein subjecting the subject to perfusion imaging comprises imaging using a PET camera or a SPECT camera.

113. A method of assessing viability of the blood-brain barrier in a neurodegenerative disease in a subject, comprising:
administering to a subject a compound, chelate, complex or salt of any one of aspects 1-46 or 76-102; and subjecting the subject to imaging of the brain, wherein the complex or salt comprises a radioactive metal isotope.

114. A method of assessing viability of the blood-brain barrier in a neurodegenerative disease in accordance with aspect 113, wherein the imaging comprises PET scanning.

115. A method of assessing viability of the blood-brain barrier in a neurodegenerative disease in accordance with aspect 113, wherein the imaging comprises SPECT imaging.

116. A method of imaging a tumor in a subject, comprising:
administering to the subject a complex or salt of any one of aspects 1-43 or 66-97; and detecting the distribution of the complex or salt in the subject, wherein the complex or salt comprises a radioactive metal isotope.

117. A method of imaging a tumor in a subject in accordance with aspect 116, wherein the detecting distribution of the complex or salt comprises imaging drug-sensitive (−Pgp) and drug resistant (+Pgp) tumors in the subject.

DETAILED DESCRIPTION

As used herein, a "compound" is an organic covalent structure.

As used herein, a "chelate" is a covalent structure than can bond non-covalently with a cation.

As used herein, a "complex" is a covalent structure or chelate bonded with a cation.

As used herein, a "salt" is a complex combined with an anion.

As used herein, a "metal salt" comprises a metal cation and an anion. The anion can be organic or inorganic.

As used herein, with regard to chemistry procedures, "contacting" can include mixing, combining, stirring in, or the like, and can include, e.g., mixing chemicals under conditions that promote or result in a chemical reaction.

In some configurations, a gallium(III) agent such as 1, 1A or 1B incorporating an organic scaffold comprising six donor atoms, e.g. 2 or 2A, can result in an octahedral geometry.

In various aspects, compounds, chelates, complexes and salts of the present teaching can be used as tracers for imaging cardiac tissue in mammals such as humans. In various aspects, compounds, chelates, complexes and salts of the present teaching can be used as fertilizer. In some configurations, a complex or salt of the present teachings can comprise an iron ion, and can be used to provide iron to plants. In some configurations, a complex or salt of the present teachings can comprise an iron ion, and can be useful in the treatment of anemia.

The present teachings, including descriptions provided in the Examples, are not intended to limit the scope of any claim. Unless specifically presented in the past tense, an example can be a prophetic or an actual example. The examples are not intended to limit the scope of the aspects. The methods described herein utilize laboratory techniques well known to skilled artisans, and guidance can be found in laboratory manuals and textbooks such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E. Using Antibodies: A Laboratory Manual, Cold Spring Harbor Laboratory Press, Cold Spring Harbor, N.Y., 1999; Hedrickson et al. Organic Chemistry 3rd edition. McGraw Hill, New York, 1970; Carruthers. W., and Coldham, I., Modern Methods of Organic Synthesis (4th Edition), Cambridge University Press, Cambridge, U.K., 2004; Curati, W. L., Imaging in Oncology, Cambridge University Press, Cambridge, U.K., 1998; Welch, M. J., and Redvanly, C. S., eds. Handbook of Radiopharmaceuticals: Radiochemistry and Applications, J. Wiley, New York, 2003.

EXAMPLES

Example 1

Figure 1:
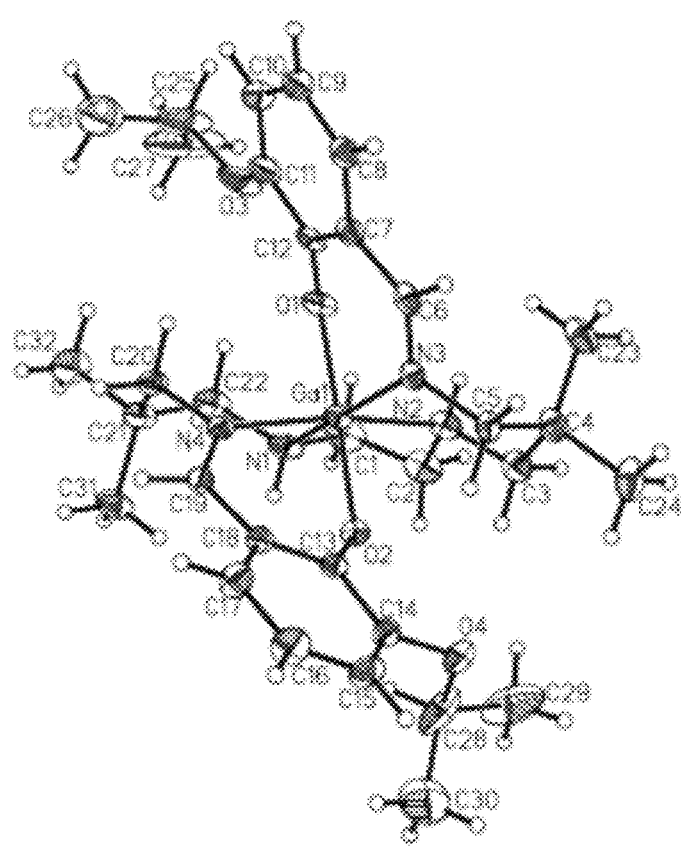
FIG. 1 presents a projection view of cationic gallium (III) complex [ENBDMP-3-isopropoxy-PI-Ga]$^+$ (I).

This Example illustrates the structure of a complex of the present teachings. The crystal structure of [ENBDMP-3-isopropoxy-PI-Ga]+ displayed in FIG. 1 shows a symmetrical engagement of the four nitrogen atoms in the equatorial plane and two axial phenolate atoms. FIG. 1 presents a projection view of cationic gallium (II) complex [ENBDMP-3-isopropoxy-PI-Ga]$^+$ (1), but without iodide (I$^-$) as the counter anion. FIG. 1 includes the crystallographic numbering scheme. Atoms are represented by thermal ellipsoids corresponding to 50% probability. $^1$H NMR, proton-decoupled $^{13}$C NMR, and HRMS analysis can also be used to validate the structure.

Example 2

Figure 2:
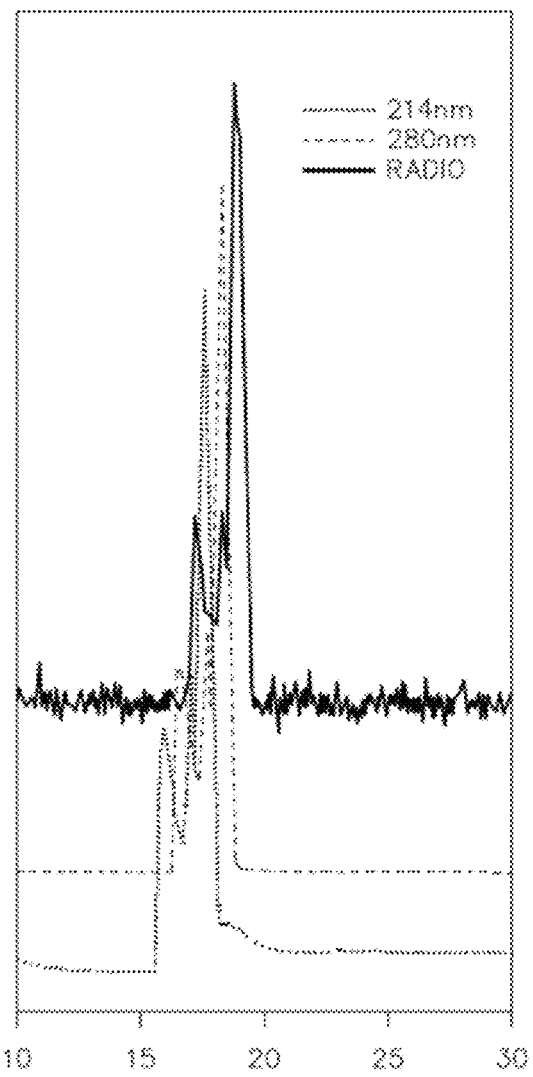
FIG. 2 presents HPLC data for [ENBDMP-3-isopropoxy-PI-$^{67}$Ga]$^+$ (1A) co-injected with the unlabeled complex 1.

This Example illustrates HPLC data confirming synthesis and radiolabeling of [ENBDMP-3-isopropoxy-PI-$^{67}$Ga]$^+$. In these experiments, the $^{67}$Ga-labeled complex (1A) was synthesized and characterized via HPLC. FIG. 2 presents HPLC data for [ENBDMP-3-isopropoxy-PI-$^{67}$Ga]$^+$ 1A co-injected with unlabeled 1. In FIG. 2, peaks have been offset for visualization.

Example 3

Figure 3:
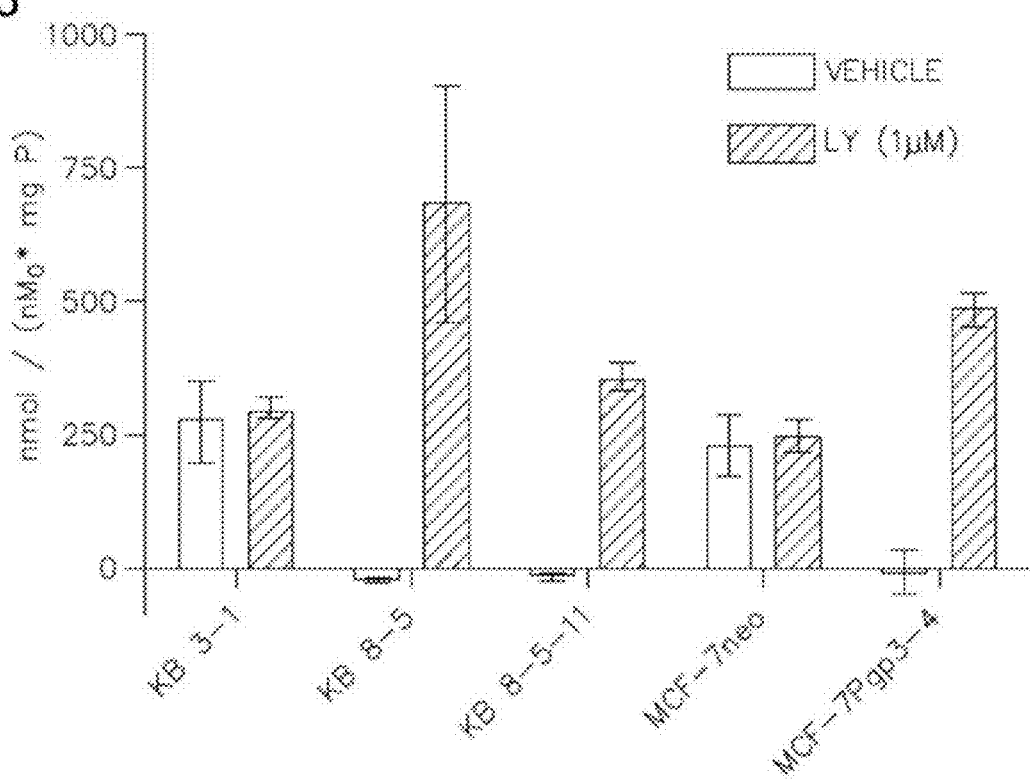
FIG. 3 presents a characterization of [ENBDMP-3-isopropoxy-PI-$^{67}$Ga]$^+$ (1A).

This Example illustrates characterization of [ENBDMP-3-isopropoxy-PI-$^{67}$Ga]$^+$ for 1A, FIG. 3 shows cellular accumulation of 1A in KB-3-1 cells (–Pgp). MCF-7 cells (–Pgp), MDR KB-8-5 (+Pgp), KB-8-5-11 (Pgp++) cells and stably transfected MCF-7/MDR1 cells as indicated. Shown is net uptake at 90 minutes (fmol (mg protein)$^{-1}$ (nM$_0$)$^{-1}$) using control buffer in the absence or presence of MDR1Pgp inhibitor LY335979 (1 µM). Each bar represents the mean of 4 determinations; line above the bar denotes +SEM.

Example 4

This Example presents in cellulo and in vivo bioassays to illustrate some functions of some disclosed complexes. In these experiments, the $^{67}$Ga-labeled salt 1A

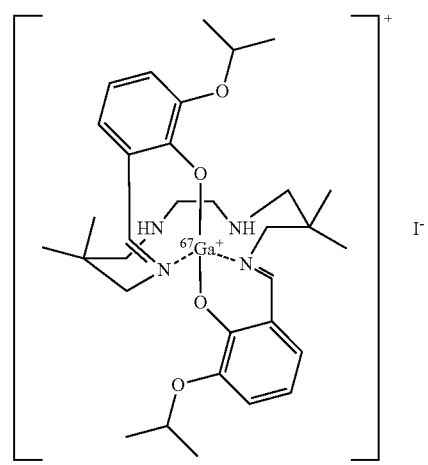

was evaluated using cell transport studies and quantitative biodistribution studies in mdr1a/1b$^{(-/-)}$ gene-deleted mice and their wild-type (WT) counterparts. In these experiments, radiolabeled $^{67}$Ga-analogue showed high accumulation in human epidermal carcinoma drug-sensitive KB-3-1 cells (Pgp$^-$) and human breast carcinoma MCF-7 (Pgp$^-$) cells, and low accumulation in MDR KB-8-5 (+Pgp), KB-8-5-11 (++Pgp) cells and stably transfected MCF-7/MDR1 (+Pgp) cells. Pgp inhibitor LY335979 (Zosuquidar trihydrochloride, Selleck Chemicals, Houston, Tex.) (1 µM), enhanced accumulation in multidrug resistant (MDR, Pgp$^+$) KB-8-5, KB-8-5-11 cells, and stably transfected MCF-7/MDR1 cells, thus demonstrating its responsiveness to Pgp-mediated functional transport activity in cellulo (FIG. 3). In mdr1a/1b$^{(-/-)}$ gene-deleted mice, the $^{67}$Ga-labelled complex showed 16-fold greater brain penetration and retention (% ID/g=0.96) compared with WT counterparts (% ID/g=0.06), 2 h post injection of 1A (Tables 1 & 2). Additionally, 1A also showed 2.6 fold higher retention in blood of mdr1a/1b$^{(-/-)}$ gene-deleted mice compared with WT counterparts (Table 1 & 2), consistent with Pgp expression in white cells of WT mice. These data indicated the ability of 1A to be transported out of cells expressing Pgp and to serve as a probe of the Pgp-mediated component of the blood-brain barrier (BBB) function.

Example 5

This Example discloses synthesis of [ENBDMP-3-isopropoxy-PI-Ga]$^+$ I$^-$ 1. The ligand (100 mg, 0.18 mmol) was dissolved in methanol (5 mL) and was treated with dropwise addition of gallium(II) acetylacetonate (66.2 mg, 0.18 mmol) dissolved in methanol. The contents were refluxed for 3 h. Then, potassium iodide (30 mg, 0.18 mmol) dissolved in hot water (0.5 mL) was added and the reaction mixture was refluxed further for 15 min, brought to room temperature slowly. Slow evaporation over a few days yielded crystalline material, 30% yield. $^1$H NMR (300 MHz, DMSO-d6) δ: 0.79 (s, 6H), 0.96 (s, 6H), 1.30-1.33 (dd, 12H), 2.63 (d, 2H), 2.79 (d, 4H) 2.94 (br, s, 21), 3.61-3.75 (m 4H), 4.63 (quintet, 2H), 4.79 (br, s, 2H), 6.62 (t, 2H), 6.87 (d, 2H), 7.04 (d, 2H), 8.18 (s, 2H); $^{13}$C NMR (300 MHz, DMSO-d6) δ: 22.0, 22.1, 22.2, 26.2, 35.6, 47.7, 59.2, 68.9, 69.5, 115.7, 119.2, 119.5, 125.8, 148.6, 158.1, 170.3. MS (HRESI) Calcd for [C32H48N4O4Ga]+; 621.2926. found: m/z=621.2930 and Calcd for [$^{13}$C$_{32}$H$_{48}$N$_4$O$_4$Ga]$^+$; 622.2959. found: m/z=622.2967.

Example 6

This Example discloses preparation of preparation of $^{67}$Ga-metalloprobe 1A.

Radiolabeled $^{67}$Ga-metalloprobe was synthesized by following a procedure described earlier and slight modifications. $^{67}$Ga was obtained as a commercial citrate salt in water (Mallinckrodt, Inc., Saint Louis, Mo.), converted into chloride, and finally into $^{67}$Ga(acetylacetonate)$_3$ by reacting with acetylacetone using standard procedures. Radiolabeled $^{67}$Ga-metalloprobes were obtained through a ligand exchange reaction involving either $^{67}$Ga(acetylacetonate)$_3$ or $^{67}$GaCl$_3$ and hexadentate(2) or heptadentate (2A) Schiff-base ligands dissolved in ethanol at 100° C. for 40 min. Reaction was followed using thin-layer chromatography plates (C-18) employing a radiometric scanner (Bioscan), using an eluent mixture of ethanol/saline (90/10; $R_f$: 0.23). Finally, $^{67}$Ga-metalloprobe 1A was purified by radio-HPLC using a Vydac TP C-18 reversed-phase column (10 µm, 300 Å) (Grace Discovery Sciences, Deerfield, Ill.) using an eluent mixture of ethanol and saline as a gradient system. The fraction eluting at a retention time of 16.8 min (1A) was collected, concentrated, and employed for bioassays.

Example 7

This Example discloses preparation of $^{68}$Ga-metalloprobe 1B.

Radiolabeled $^{68}$Ga-metalloprobe was synthesized by following a procedure described earlier and slight modifications. $^{68}$Ga was obtained from the generator as its chloride salt, converted into $^{68}$Ga(acetylacetonate)$_3$ by reacting with acetylacetone (0.01% solution in ethanol) using standard procedures. Radiolabeled $^{67}$Ga-metalloprobe were obtained through a ligand exchange reaction involving either $^{68}$Ga (acetylacetonate)$_3$ or $^{68}$GaCl$_3$ and hexadentate or heptadentate Schiff-base ligands (2 or 2A) dissolved in ethanol at 100° C. for 40 min. Reaction was followed using thin-layer chromatography plates (C-18) employing a radiometric scanner (Bioscan), using an eluent mixture of ethanol/saline (90/10; Rf: 0.23). Finally, $^{68}$Ga-metalloprobe 1B was purified by radio-HPLC using Vydac TP C-18 reversed-phase column (10 µm, 300 Å) using an eluent mixture of ethanol and saline as a gradient system. The fraction eluting at a retention time of 16.8 min (1B) was collected, concentrated, and employed for bioassays.

Example 8

This Example discloses preparation of 1,2-ethylenediamino-bis[1-{(3-isopropoxyphenylene-2-ol)methylenimino-2,2-dimethyl}propane](2).

To obtain 2, the starting precursor amine, 1,2-ethylenediamino-bis(2,2-dimethylaminopropane) was synthesized as described (Sivapackiam, J., et al., Dalton Transactions 39, 5842-5850, 2010). Additionally, the second starting precursor, 2-hydroxy-3-isopropoxy-1-benzaldehyde was also obtained using a procedure described below:

3-isopropoxyphenol (1.34 mmol), anhydrous magnesium chloride (6.73 mmol), and anhydrous triethylamine (13.4 mmol) were suspended in anhydrous acetonitrile (50 mL), and suspension was stirred for 1 h at room temperature. Then, p-formaldehyde (6.72 mmol) was added to the mixture and the contents were heated at reflux for 4 h. The reaction mixture was cooled to room temperature, hydrolyzed, acidified with 10% HCl (50 mL), and extracted with ether (3×200 mL). The combined organic extract was dried over anhydrous sodium sulfate, filtered, concentrated, and the residue was purified on silica gel GF254 (Analtech, USA) using hexane/ethyl acetate (70/30) as eluent mixture, 57% yield. $^1$H NMR (300 MHz, CDCl$_3$) δ: 1.28 (d, 611), 4.48 (quintet, 1H), 6.84 (t, 1H), 7.03-7.11 (dd, 2H), 9.81 (s, 1H), 10.87 (s, 1H); $^{13}$C NMR (75 MHz, CDCl$_3$) δ: 22.1, 72.2, 119.6, 121.4, 122.8, 125.3, 146.5, 153.0, 196.6; MS (HRESI) Calcd for $[C_{10}H_{12}O_3]^+$: 163.0754. found: 163.0759.

Finally, for obtaining 2, starting precursors, 2-Hydroxy-3-isopropoxy-1-benzaldehyde (1.80 mmol) and 1,2-ethylenediamino-bis(2,2-dimethylaminopropane) (0.90 mmol) were dissolved in ethanol (10 mL) refluxed for 45 min, and purified by methods described previously. $^1$H NMR (300 MHz, CDCl$_3$) δ: 0.90 (s, 12H), 1.39 (d, 12H), 2.05-2.80 (m, 12H), 2.75 (bs, 2H) 4.60 (q, 2H), 6.80 (t, 2H), 6.850-6.95 (dd, 4H), 7.45 (d, 2H), 8.28 (s, 2H); MS (HRESI) Calcd for [C32H50N4O4]; 554.3832. found: m/z=555.3918.

Example 9

This Example discloses a kit formulation of ligands 2 and 2A.

2 or 2A (10 mg) was dissolved in ethanol (500 µl) and treated with potassium acetate (1 mM, 15 ml, pH 5.5) and contents were stirred in an argon flushed amber colored vial. The mixture was filtered through a nylon syringe filter (0.2 µM), and aliquoted into amber colored sterile vials (5 ml), and lyphilized at −50° C. These kits were stored in a refrigerator for 3 months without any appreciable decomposition and used for preparation of 1 and its $^{67}$Ga-labeled counterpart (1A) or $^{68}$Ga-counterpart (1B) as described above.

Example 10

This example discloses formation and analysis of a crystal.

In these experiments, crystals suitable for X-ray crystallography were grown by dissolving 1 in refluxing methanol, slowly bringing solution to room temperature and extremely slow concentration of the methanol solution overnight. A single crystal with approximate dimensions 0.28×0.18×0.17 mm; was mounted on a glass fiber in a random orientation. Preliminary examination and data collection were performed using a Bruker Kappa Apex II (Charge Coupled Device (CCD) Detector system, Bruker AXS, Inc., Madison, Wis.) single crystal X-Ray diffractometer, equipped with an Oxford Cryostream LT device.

Example 11

This example discloses bioassays.

All bioassays were performed as described in earlier publications. (Sivapackiam, J., et al., Dalton Transactions 39, 5842-5850, 2010; Harpstrite, S. E., et al., J. Inorg. Biochem. 101, 1347-1353, 2007; Sharma, V., et al., J. Nucl. Med. 46, 354-364 2005).

Gallium(III) agent (1) incorporates a compound possessing six donor atoms and results in an octahedral geometry (FIG. 1). Suitable crystals for analysis were obtained via slow evaporation of a methanol solution of the gallium(III) complex 1. Crystal structure showed a symmetrical engagement of the four equatorial nitrogen atoms and two phenolic oxygen atoms. Upon chemical characterization using routine analytical tools such as $^1$H NMR, proton-decoupled $^{13}$C NMR, and HRMS analysis, the agent was validated via multiple bioassays in cellulo and in vivo. The radiolabeled $^{67}$Ga-agent (1A) was obtained via ligand-exchange reaction using $^{67}$Ga(acac)$_3$ and ligand 2 or 2A. The product was purified via HPLC using a γ-radiodetector (FIG. 2) and characterized via multiple bioassays. $^{67}$Ga-labeled counterpart (1A) was evaluated via cell transport studies using human epidermal carcinoma (Pgp$^-$; Pgp$^+$) cells and quantitative biodistribution studies in mdr1a/1b$^{(-/-)}$ gene-deleted mice and their wild-type (WT) counterparts. Radiolabeled $^{67}$Ga-analogue (1A) showed high accumulation in human epidermal carcinoma drug-sensitive KB-3-1 cells (Pgp$^-$), human breast carcinoma MCF-7 (Pgp$^-$) cells; an inhibitor (LY335979, 1 μM) induced accumulation in multidrug resistant (MDR, Pgp$^-$) KB-8-5, KB-8-5-11 cells, and stably transfected MCF-7/MDR1 cells, thus demonstrating its ability to interrogate Pgp-mediated functional transport activity in cellulo (FIG. 3). In mdr1a/1b$^{(-/-)}$ gene-deleted mice, the $^{67}$Ga-metalloprobe showed 16-fold greater brain uptake and retention compared with WT counterparts (Table 1 and Table 2). Additionally, the agent permeated the heart tissue accompanied by a facile clearance from the livers of mice (Table 1 and Table 2) and rats (Table 3), thus leading to extremely high target to background ratios (Table 4 and Table 5), showing the potential of the agent for heart perfusion imaging. Thus, molecular imaging of the functional transport activity of MDR1 Pgp (ABCB1) using the disclosed 67/68Ga-metalloprobe enables noninvasive monitoring of the blood-brain barrier in neurodegenerative diseases, assessment of tumors to stratify patient populations for chemotherapeutic treatments, as well as probe the presence or absence of Pgp tissues in vivo, probing depolarization of the membrane potential, and can also provide a myocardial perfusion PET/SPECT imaging agent. Additionally, our synthesis, purification, and formulation of the agent could be accomplished in less than 60 minutes.

Example 12

Figure 4:
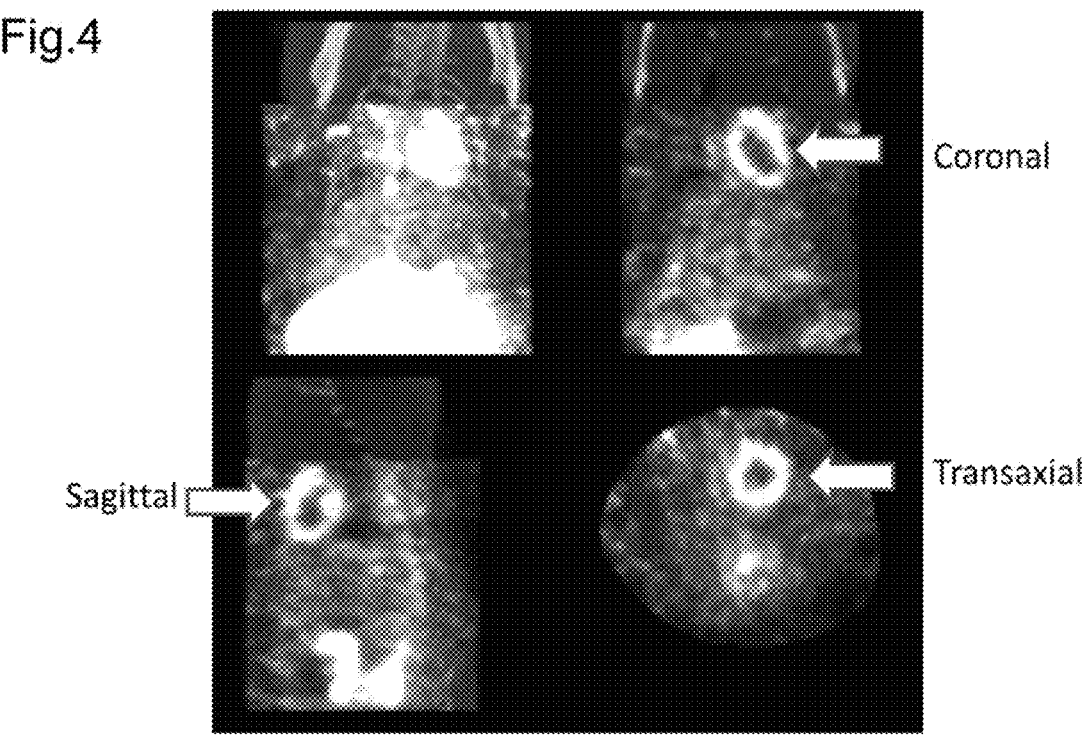
FIG. 4 illustrates NanoSPECT/CT imaging using [ENBDMP-3-isopropoxy-PI-$^{67}$Ga]$^+$ (1A) 30 min post injection into a rat.
Figure 5:
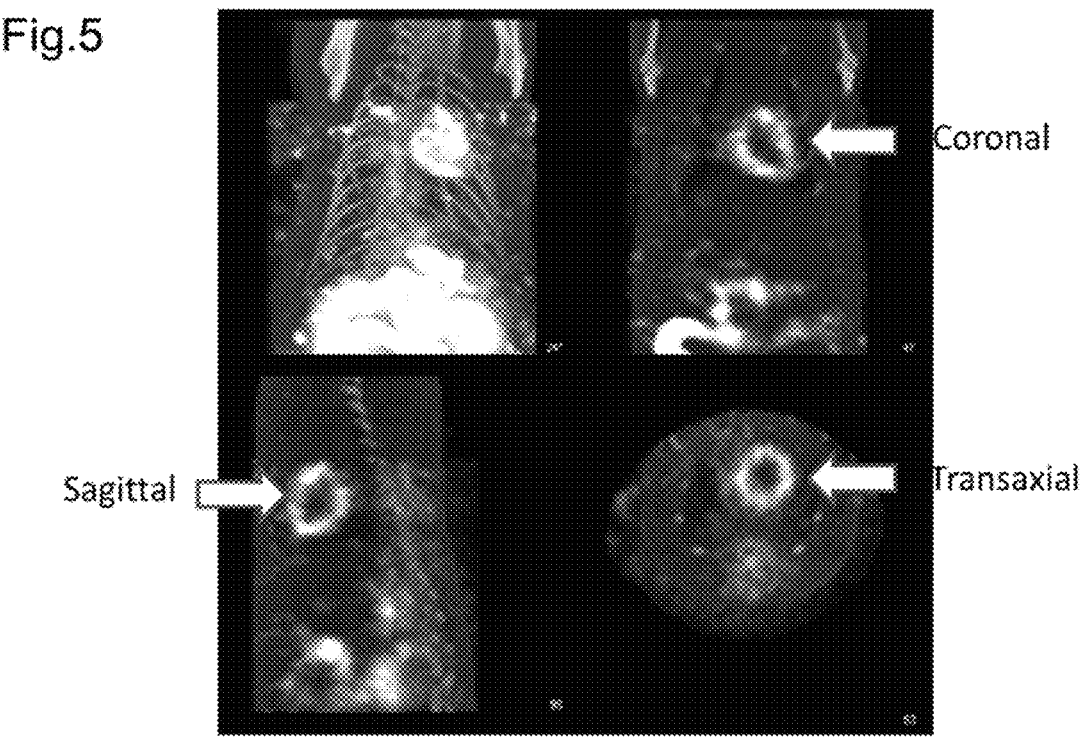
FIG. 5 illustrates NanoSPECT/CT imaging using [ENBDMP-3-ispropoxy-PI-$^{67}$Ga]$^+$ (1A) 250 min post injection into a rat.

This Example illustrates NanoSPECT/CT imaging using the $^{67}$Ga-radiopharmaceutical (1A). In these experiments. $^{67}$Ga-radiopharmaceutical 1A was injected intravenously into a rat tail-vein: NanoSPECT/CT images were obtained 30 min. (FIG. 4) and 250 min. (FIG. 5) post-injection. The arrows indicate heart uptake.

Example 13

Figure 6:
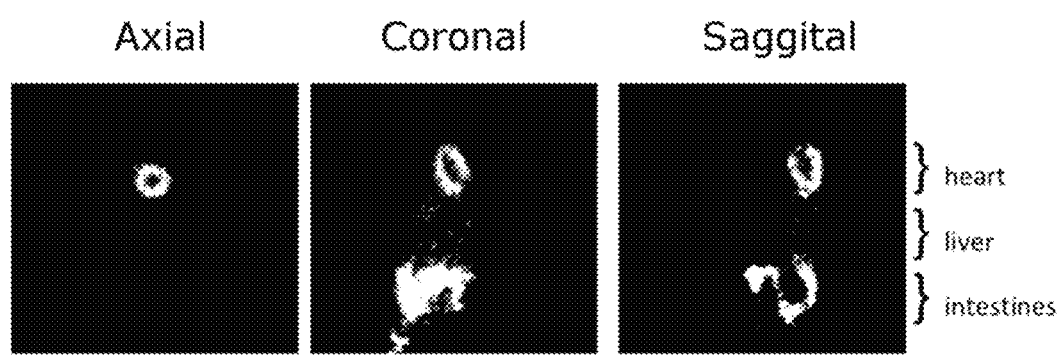
FIG. 6 illustrates MicroPET imaging of myocardial perfusion using [ENBDMP-3-isopropoxy-PI-$^{68}$Ga]$^+$ (1B) 60 min post injection into a rat.

This Example illustrates MicroPET imaging of myocardial perfusion in a rat. In these experiments, $^{68}$Ga-radiopharmaceutical 1B was injected intravenously into a rat tail-vein; MicroPET images were obtained 60 min. (FIG. 6) post-injection. Note low level of signal from liver compared to the heart.

All references cited herein are incorporated by reference each in its entirety. Tables

TABLE 1

Biodistribution data (% ID/g) for $^{67}$Ga-Agent 1a in WT mice (n = 3).

| % ID/g | time(min) P.I. | | | | | | | |
|---|---|---|---|---|---|---|---|---|
| | 5 | | 15 | | 60 | | 120 | |
| | Average | SEM | Average | SEM | Average | SEM | Average | SEM |
| blood | 1.26 | 0.33 | 0.29 | 0.04 | 0.10 | 0.01 | 0.07 | 0.01 |
| liver | 44.95 | 1.24 | 33.80 | 1.80 | 7.44 | 0.44 | 2.90 | 0.24 |

TABLE 1-continued

Biodistribution data (% ID/g) for $^{67}$Ga-Agent 1a in WT mice (n = 3).

| % ID/g | time(min) P.I. | | | | | | | |
|---|---|---|---|---|---|---|---|---|
| | 5 | | 15 | | 60 | | 120 | |
| | Average | SEM | Average | SEM | Average | SEM | Average | SEM |
| kidneys | 81.04 | 17.46 | 83.46 | 10.00 | 93.35 | 14.49 | 67.91 | 5.59 |
| heart | 9.21 | 1.64 | 8.37 | 0.98 | 11.98 | 0.74 | 9.81 | 1.90 |
| brain | 0.14 | 0.01 | 0.12 | 0.02 | 0.09 | 0.01 | 0.06 | 0.01 |

TABLE 2

Biodistribution data (% ID/g) for $^{67}$Ga-Agent 1a in mdr 1a/1b (—/—) (dKO) mice (n = 3).

| % ID/g | time(min) P.I. | | | | | | | |
|---|---|---|---|---|---|---|---|---|
| | 5 | | 15 | | 60 | | 120 | |
| | Average | SEM | Average | SEM | Average | SEM | Average | SEM |
| blood | 1.54 | 0.22 | 0.64 | 0.10 | 0.34 | 0.03 | 0.19 | 0.05 |
| liver | 46.34 | 3.71 | 46.45 | 3.42 | 42.54 | 5.61 | 29.82 | 2.66 |
| kidneys | 86.12 | 4.33 | 84.19 | 7.62 | 95.60 | 10.38 | 115.23 | 10.09 |
| heart | 17.02 | 2.42 | 10.59 | 0.58 | 14.61 | 0.64 | 20.29 | 4.45 |
| brain | 1.05 | 0.03 | 0.65 | 0.08 | 0.99 | 0.10 | 0.96 | 0.13 |

TABLE 3

Biodistribution data (% ID/g) for $^{67}$Ga-Agent 1a in rats (n = 3).

| % ID/g | time(min) P.I. | | | | | | | |
|---|---|---|---|---|---|---|---|---|
| | 5 | | 15 | | 60 | | 120 | |
| | Average | SEM | Average | SEM | Average | SEM | Average | SEM |
| blood | 0.175 | 0.016 | 0.041 | 0.003 | 0.028 | 0.003 | 0.012 | 0.002 |
| lung | 0.814 | 0.069 | 0.626 | 0.018 | 0.559 | 0.023 | 0.591 | 0.006 |
| liver | 2.615 | 0.148 | 0.657 | 0.029 | 0.328 | 0.017 | 0.203 | 0.028 |
| kidneys | 8.142 | 0.620 | 5.168 | 0.144 | 4.201 | 0.101 | 3.543 | 0.108 |
| heart | 1.443 | 0.046 | 1.306 | 0.038 | 1.386 | 0.026 | 1.516 | 0.013 |
| brain | 0.024 | 0.003 | 0.015 | 0.001 | 0.018 | 0.001 | 0.016 | 0.001 |

TABLE 4

Heart to Tissue Ratio of $^{67}$Ga-Agent 1a in rats (n = 3).

| % ID/g | time(min) P.I. | | | | | |
|---|---|---|---|---|---|---|
| | 5 | | 60 | | 120 | |
| | Average | SEM | Average | SEM | Average | SEM |
| Heart/Blood | 8.386 | 0.017 | 49.677 | 4.275 | 138.825 | 32.596 |
| Heart/Liver | 0.554 | 0.069 | 4.246 | 0.166 | 7.782 | 1.127 |

TABLE 5

Heart to Tissue Ratio of $^{67}$Ga-Agent 1a in WT mice (n = 3).

| % ID/g | time(min) P.I. | | | | | |
|---|---|---|---|---|---|---|
| | 5 | | 60 | | 120 | |
| | Average | SEM | Average | SEM | Average | SEM |
| Heart/Blood | 7.772 | 1.13 | 126.918 | 18.45 | 146.618 | 24.53 |
| Heart/Liver | 0.206 | 0.04 | 1.617 | 0.12 | 3.526 | 0.88 |

What is claimed is:

1. A compound comprising a structure

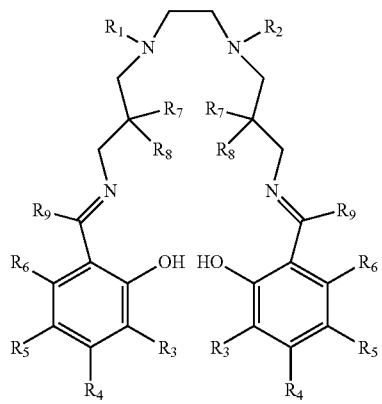

Wherein each of $R_1$ and $R_2$ is H; each of $R_7$ and $R_8$ is methyl; each $R_3$ is isopropoxy; each of $R_4$, $R_5$ and $R_6$ is H; and each $R_9$ is H.

2. A salt of structure

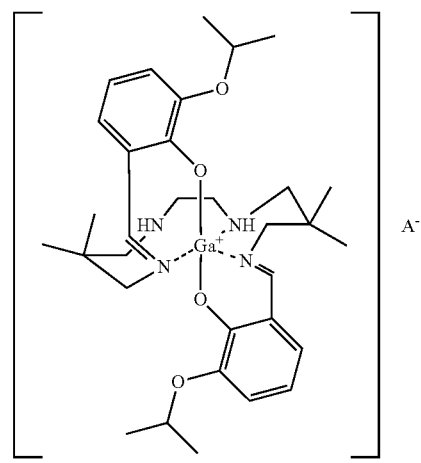

wherein A− is an anion.

3. The salt in accordance with claim 2, wherein the anion is an I−.

4. The salt in accordance with claim 2, wherein the Ga+ is a $^{67}$Ga+.

5. The salt in accordance with claim 2, wherein the Ga+ is a $^{68}$Ga+.

6. The salt in accordance with claim 2, wherein the anion is an I− and the Ga+ is a $^{68}$Ga+.

* * * * *

UNITED STATES PATENT AND TRADEMARK OFFICE
CERTIFICATE OF CORRECTION

PATENT NO. : 9,579,408 B2
APPLICATION NO. : 13/984723
DATED : February 28, 2017
INVENTOR(S) : Vijay Sharma et al.

It is certified that error appears in the above-identified patent and that said Letters Patent is hereby corrected as shown below:

In the Specification

Column 1 paragraph 1, should read:
Statement of Government Support
This invention was made with government support under AG033328 and CA094056 and HL111163 awarded by the National Institutes of Health. The government has certain rights in the invention.

Signed and Sealed this
Twelfth Day of February, 2019

Andrei Iancu
*Director of the United States Patent and Trademark Office*